(12) United States Patent
Rezaei

(10) Patent No.: US 12,423,815 B2
(45) Date of Patent: Sep. 23, 2025

(54) METHODS AND SYSTEMS FOR REAL TIME EXTRACTION OF CROSSTALK IN ILLUMINATION EMITTED FROM REACTION SITES

(71) Applicant: ILLUMINA, INC., San Diego, CA (US)

(72) Inventor: Mohsen Rezaei, Brown Deer, WI (US)

(73) Assignee: ILLUMINA, INC., San Diego, CA (US)

( * ) Notice: Subject to any disclaimer, the term of this patent is extended or adjusted under 35 U.S.C. 154(b) by 317 days.

(21) Appl. No.: 17/858,268

(22) Filed: Jul. 6, 2022

(65) Prior Publication Data

US 2023/0027409 A1    Jan. 26, 2023

Related U.S. Application Data

(60) Provisional application No. 63/221,236, filed on Jul. 13, 2021.

(51) Int. Cl.
*G06T 7/00* (2017.01)
*G01N 33/58* (2006.01)
*G06T 5/73* (2024.01)
*G16B 30/00* (2019.01)

(52) U.S. Cl.
CPC ......... *G06T 7/0014* (2013.01); *G01N 33/582* (2013.01); *G06T 5/73* (2024.01); *G16B 30/00* (2019.02); *G06T 2207/20224* (2013.01)

(58) Field of Classification Search
CPC ............... C12Q 1/6869; G01N 33/582; G06T 2207/20224; G06T 2207/30072; G06T 5/73; G06T 7/0014; G16B 30/00
See application file for complete search history.

(56) References Cited

U.S. PATENT DOCUMENTS

| | | | |
|---|---|---|---|
| 5,641,658 | A | 6/1997 | Adams et al. |
| 6,090,592 | A | 7/2000 | Adams et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |

(Continued)

FOREIGN PATENT DOCUMENTS

| | | |
|---|---|---|
| CN | 103927740 A | 7/2014 |
| CN | 104574423 A | 4/2015 |

(Continued)

OTHER PUBLICATIONS

Clenmens, "Flow Imaging", 2002. (Year: 2002).*

(Continued)

*Primary Examiner* — Ruiping Li
(74) *Attorney, Agent, or Firm* — FROST BROWN TODD LLP

(57) ABSTRACT

Biosensor including an array of reaction sites and corresponding light sensors may experience crosstalk in which photons from one reaction site are detected by neighbors of its corresponding light sensor, and such crosstalk may be corrected using sharpening kernels corresponding to the sensors in the array. Such sharpening kernels may be derived from point spread functions, which may be determined in real time analysis based on images captured during sequencing.

19 Claims, 17 Drawing Sheets

(56) References Cited

U.S. PATENT DOCUMENTS

| | | |
|---|---|---|
| 7,329,492 B2 | 2/2008 | Hardin et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 7,595,883 B1 | 9/2009 | El Gamal et al. |
| 8,396,320 B2 | 3/2013 | Allebach et al. |
| 8,638,096 B2 | 1/2014 | Zhang et al. |
| 8,830,363 B2 | 9/2014 | Jang |
| 9,453,258 B2 | 9/2016 | Kain et al. |
| 9,696,408 B2 | 7/2017 | Eikenberry et al. |
| 9,747,672 B2 | 8/2017 | Oniki et al. |
| 10,304,189 B2 | 5/2019 | Garcia et al. |
| 11,935,311 B2 * | 3/2024 | Egertson .............. C12Q 1/6834 |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2005/0100900 A1 | 5/2005 | Kawashima et al. |
| 2005/0244870 A1 | 11/2005 | Chee et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0108082 A1 | 5/2008 | Rank et al. |
| 2008/0234136 A1 | 9/2008 | Drmanac et al. |
| 2008/0242560 A1 | 10/2008 | Gunderson et al. |
| 2011/0059865 A1 | 3/2011 | Smith et al. |
| 2018/0060635 A1 | 3/2018 | Li et al. |
| 2019/0005351 A1 | 1/2019 | Zhou et al. |
| 2019/0333197 A1 * | 10/2019 | Kask .......................... G06T 5/40 |
| 2020/0080142 A1 | 3/2020 | Langlois et al. |

FOREIGN PATENT DOCUMENTS

| | | | |
|---|---|---|---|
| EP | 2360638 A1 * | 8/2011 | ............. G06T 5/003 |
| WO | WO 1991/006678 A1 | 5/1991 | |
| WO | WO 2004/018497 A2 | 3/2004 | |
| WO | WO 2005/065814 A1 | 7/2005 | |
| WO | WO 2006/064199 A1 | 6/2006 | |
| WO | WO 2007/010251 A2 | 1/2007 | |
| WO | WO 2007/123744 A2 | 11/2007 | |
| WO | WO 2007/135368 A2 | 11/2007 | |
| WO | WO 2012/058096 A1 | 5/2012 | |
| WO | 2020/061237 A1 | 3/2020 | |

OTHER PUBLICATIONS

Bentley, David R., et al. "Accurate whole human genome sequencing using reversible terminator chemistry." *nature* 456.7218 (2008): 53-59.

U.S. Appl. No. 61/538,294, entitled "Methods and Compositions for Nucleic Acid Sequencing," filed Sep. 23, 2011.

U.S. Appl. No. 61/619,878, entitled "Methods and Compositions for Nucleic Acid Sequencing," filed Apr. 3, 2012.

U.S. Appl. No. 62/216,125, entitled "Methods and Systems to Correct Crosstalk in Illumination Emitted from Reaction Sites," filed Jun. 29, 2021.

Brauers, Johannes, Claude Seiler, and Til Aach. "Direct PSF estimation using a random noise target." *Digital photography VI*. Vol. 7537. SPIE, 2010.

Salama, Khaled. *CMOS luminescence detection lab-on-chip: modeling, design, and characterization*. Stanford University, 2005.

Zhan, Dazhi, et al. "PSF estimation method of simple-lens camera using normal sinh-arcsinh model based on noise image pairs." *IEEE Access* 9 (2021): 49338-49353.

International Search Report and Written Opinion dated Dec. 5, 2022, for International Application No. PCT/US2022/036193, 15 pages.

* cited by examiner

1002

| $B^{1,1}$ | $B^{1,2}$ | ... | $B^{1,N}$ |
| $B^{2,1}$ | $B^{2,2}$ |     | $B^{2,N}$ |
| ⋮         |           | ⋱   | ⋮         |
| $B^{M,1}$ | $B^{M,2}$ | ... | $B^{M,N}$ |

−

1001

| $A^{1,1}$ | $A^{1,2}$ | ... | $A^{1,N}$ |
| $A^{2,1}$ | $A^{2,2}$ |     | $A^{2,N}$ |
| ⋮         |           | ⋱   | ⋮         |
| $A^{M,1}$ | $A^{M,2}$ | ... | $A^{M,N}$ |

=

1003

| $B^{1,1}-A^{1,1}$ | $B^{1,2}-A^{1,2}$ | ... | $B^{1,N}-A^{1,N}$ |
| $B^{2,1}-A^{2,1}$ | $B^{2,2}-A^{2,2}$ |     | $B^{2,N}-A^{2,N}$ |
| ⋮                 |                   | ⋱   | ⋮                 |
| $B^{M,1}-A^{M,1}$ | $B^{M,2}-A^{M,2}$ | ... | $B^{2,N}-A^{2,N}$ |

FIG. 10 odd_odd

| 0.05 | 0.53 | 0.75 | 0.46 | 0.54 |
|------|------|------|------|------|
| 0.78 | 2.9  | 8.8  | 3.6  | 1    |
| 1.4  | 6.3  | 47   | 7.9  | 0.33 |
| 0.81 | 3.4  | 6.6  | 2.6  | 0.84 |
| 0.17 | 0.55 | 1.4  | 0.87 | 0.45 | odd_even

| 0.34 | 0.15 | 0.38 | 0.91 | 0.32  |
|------|------|------|------|-------|
| 0.66 | 3.2  | 9.6  | 2.7  | 0.65  |
| 1    | 8.5  | 48   | 6.3  | 0.69  |
| 0.73 | 2.5  | 6.5  | 3.6  | 0.46  |
| 0.16 | 0.55 | 1.4  | 0.92 | 0.011 | even_odd

| 0.27 | 0.92 | 0.93 | 0.32 | 0.37 |
|------|------|------|------|------|
| 0.76 | 4    | 7    | 2.3  | 0.29 |
| 1.6  | 6.1  | 46   | 7.7  | 0.36 |
| 0.77 | 2.8  | 8.9  | 3.4  | 0.61 |
| 0.7  | 0.96 | 1.2  | 1    | 0.44 | even_even

| 0.66 | 0.63 | 1.4  | 1.2  | 0.81 |
|------|------|------|------|------|
| 0.72 | 2.7  | 0.69 | 3.4  | 1.1  |
| 1    | 7.9  | 44   | 6.2  | 1    |
| 1.2  | 3.2  | 9.6  | 3    | 0.71 |
| 0.16 | 0.57 | 0.84 | 0.73 | 0.27 |

FIG. 16

METHODS AND SYSTEMS FOR REAL TIME EXTRACTION OF CROSSTALK IN ILLUMINATION EMITTED FROM REACTION SITES

This application claims the benefit of and priority to U.S. Provisional Patent Application Ser. No. 63/221,236, filed Jul. 13, 2021, entitled "Methods and Systems for Real Time Extraction of Crosstalk in Illumination Emitted from Reaction Sites," the disclosure of which is incorporated by reference herein.

BACKGROUND

Aspects of the present disclosure relate generally to biological or chemical analysis and more particularly to systems and methods using light sensors for biological or chemical analysis.

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and require a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide-semiconductor (CMOS) detector) that does not require a large optical assembly to detect the fluorescent emissions. However, such systems may have some limitations. For example, as the density of the analytes increases, it becomes increasingly challenging to manage or account for unwanted light emissions from adjacent analytes (e.g., crosstalk).

SUMMARY OF THE INVENTION

Described herein are devices, systems, and methods for determining point spread functions such as may be used in compensating for crosstalk which may be encountered in systems which perform optical analysis, such as bioassay systems.

An implementation relates to a method comprising obtaining a plurality of analysis images of light emitted during sequencing of a biological sample; obtaining noise dependencies by performing acts comprising, for each location in a point spread function which comprises a plurality of locations, calculating a noise correlation for that location, wherein the noise correlation is a correlation between noise in a first plurality of measurements and noise in a second plurality of measurements, wherein: each measurement from the first plurality of measurements is captured by a sensor whose position relative to a corresponding sensor which captured a measurement from the second plurality of measurements is the same as that location's position in the point spread function relative to a center of the point spread function; and each measurement from the first plurality of measurements and the second plurality of measurements measures light emitted during sequencing of the biological sample from the plurality of analysis images; populating the point spread function based on the noise dependencies; generating a sharpening kernel based on the point spread function; obtaining a plurality of sharpened images by applying the sharpening kernel to the plurality of analysis images; one or more times, repeating: obtaining noise dependencies; populating the point spread function; generating the sharpening kernel; and obtaining the plurality of sharpened images; wherein, on each repetition, the plurality of analysis images for that repetition of obtaining noise dependencies is the plurality of sharpened images from a most recent preceding application of the sharpening kernel; identifying a sharpening kernel generated on a repetition as an optimal sharpening kernel; and applying the optimal sharpening kernel to compensate for crosstalk in images subsequently captured while sequencing the biological sample.

In some implementations such as described in the second paragraph of this summary, repeating populating the point spread function comprises: generating a dependency matrix having dimensions equal to those of the point spread function by, for each location in the point spread function, populating a corresponding location in the dependency matrix with a most recently obtained dependency for that location; multiplying the dependency matrix by a scalar constant; and adding a result of multiplying the dependency matrix by the scalar constant to a most recently populated preceding point spread function.

In some implementations such as described in the preceding paragraph, the scalar constant has a value greater than or equal to 0.08, and less than or equal to 0.12.

In some implementations such as described in the second paragraph of this summary, identifying the optimal sharpening kernel comprises: determining, for each repetition, a signal to noise ratio obtained by applying the sharpening kernel generated on that repetition to the plurality of analysis images; and identifying the sharpening kernel from which a highest signal to noise ratio is obtained as the optimal sharpening kernel.

In some implementations such as described in the preceding paragraph of this summary, determining, for each repetition, the signal to noise ratio comprises calculating a sharpness of the plurality of sharpened images obtained on that repetition.

In some implementations such as described in the second paragraph of this summary, obtaining noise dependencies comprises obtaining a noise map based on subtracting a first image from the plurality of analysis images from a second image from the plurality of analysis images.

In some implementations such as described in the preceding paragraph of this summary, obtaining noise dependencies comprises dividing the noise map into a plurality of units, wherein each unit is a matrix of values having dimensions at least as great as those of the point spread function; for each location in the point spread function, obtaining the noise dependency for that location comprises calculating a correlation between a first set of values and a second set of values, wherein: the first set of values comprises, for each unit from the plurality of units, a value at a first location in that unit; and the second set of values comprises, for each unit from the plurality of units, a value at a second location in that unit, wherein the first location for the value from that unit in the first set of values has a position relative to the second location that is the same as that location's position in the point spread function relative to the center of the point spread function.

In some implementations such as described in either of the preceding two paragraphs of this summary, the first image from the plurality of analysis images is an image captured from a first sequencing cycle; and the second image from the plurality of analysis images is an image from a second sequencing cycle.

In some implementations such as described in the second paragraph of this summary, each image from the plurality of analysis images comprises an image from a different sequencing cycle; the plurality of analysis images comprises more than two images; obtaining noise dependencies comprises: obtaining a plurality of intermediate correlations, wherein each of the intermediate correlations corresponds to two analysis images from the plurality of analysis images, and wherein each of the plurality of intermediate correlations is obtained based on: obtaining an intermediate map for that intermediate correlation by subtracting one of the analysis images corresponding to that intermediate correlation from the other analysis image corresponding to that intermediate correlation; dividing the intermediate map for that intermediate correlation into a plurality of units, wherein each unit is a matrix of values having dimensions at least as great as those of the point spread function; for each location in the point spread function, calculating a correlation between a first set of values and a second set of values, wherein: the first set of values comprises, for each unit from the plurality of units, a value at a first location in that unit; and the second set of values comprises, for each unit from the plurality of units, a value at a second location in that unit, wherein the first location for the value from that unit in the first set of values has a position relative to the second location that is the same as that location's position in the point spread function relative to the center of the point spread function; determining the set of noise dependencies based on the plurality of intermediate correlations.

In some implementations such as described in the second paragraph of this summary, wherein obtaining noise dependencies, populating the point spread function, generating the sharpening kernel, and obtaining the plurality of sharpened images are repeated between two and eight times.

An implementation relates to a system comprising a sensor array; a processor to: obtain a plurality of analysis images of light emitted during sequencing of a biological sample; obtain noise dependencies by performing acts comprising, for each location in a point spread function which comprises a plurality of locations, calculating a noise correlation for that location, wherein the noise correlation is a correlation between noise in a first plurality of measurements and noise in a second plurality of measurements, wherein: each measurement from the first plurality of measurements is captured by a sensor from the sensor array whose position relative to a corresponding sensor in the sensor array which captured a measurement from the second plurality of measurements is the same as that location's position in the point spread function relative to a center of the point spread function; and each measurement from the first plurality of measurements and the second plurality of measurements measures light emitted during sequencing of the biological sample from the plurality of analysis images; populate the point spread function based on the noise dependencies; generate a sharpening kernel based on the point spread function; obtain a plurality of sharpened images by applying the sharpening kernel to the plurality of analysis images; one or more times, repeat: obtaining noise dependencies; populating the point spread function; generating the sharpening kernel; and obtaining the plurality of sharpened images; wherein, on each repetition, the plurality of analysis images for that repetition of obtaining noise dependencies is the plurality of sharpened images from a most recent preceding application of the sharpening kernel; identify a sharpening kernel generated on a repetition as an optimal sharpening kernel; and apply the optimal sharpening kernel to compensate for crosstalk in images subsequently captured while sequencing the biological sample.

In some implementations such as described in the preceding paragraph, repeating populating the point spread function comprises: generating a dependency matrix having dimensions equal to those of the point spread function by, for each location in the point spread function, populating a corresponding location in the dependency matrix with a most recently obtained dependency for that location; multiplying the dependency matrix by a scalar constant; and adding a result of multiplying the dependency matrix by the scalar constant to a most recently populated preceding point spread function.

In some implementations such as described in the preceding paragraph, the scalar constant has a value greater than or equal to 0.08, and less than or equal to 0.12.

In some implementations such as described in twelfth paragraph of this summary, identifying the optimal sharpening kernel comprises: determining, for each repetition, a signal to noise ratio obtained by applying the sharpening kernel generated on that repetition to the plurality of analysis images; and identifying the sharpening kernel from which a highest signal to noise ratio is obtained as the optimal sharpening kernel.

In some implementations such as described in the preceding paragraph, determining, for each repetition, the signal to noise ratio comprises calculating a sharpness of the plurality of sharpened images obtained on that repetition.

In some implementations such as described in the twelfth paragraph of this summary, obtaining noise dependencies comprises obtaining a noise map based on subtracting a first image from the plurality of analysis images from a second image from the plurality of analysis images.

In some implementations such as described in the preceding paragraph, obtaining noise dependencies comprises dividing the noise map into a plurality of units, wherein each unit is a matrix of values having dimensions at least as great as those of the point spread function; for each location in the point spread function, obtaining the noise dependency for that location comprises calculating a correlation between a first set of values and a second set of values, wherein: the first set of values comprises, for each unit from the plurality of units, a value at a first location in that unit; and the second set of values comprises, for each unit from the plurality of units, a value at a second location in that unit, wherein the first location for the value from that unit in the first set of values has a position relative to the second location that is the same as that location's position in the point spread function relative to the center of the point spread function.

In some implementations such as described in either of the preceding two paragraphs, the first image from the plurality of analysis images is an image from a first sequencing cycle; and the second image from the plurality of analysis images is an image from a second sequencing cycle.

In some implementations such as described in the twelfth paragraph of this summary, each image from the plurality of analysis images comprises an image from a different sequencing cycle; the plurality of analysis images comprises more than two images; obtaining noise dependencies comprises: obtaining a plurality of intermediate correlations, wherein each of the intermediate correlations corresponds to two analysis images from the plurality of analysis images, and wherein each of the plurality of intermediate correlations is obtained based on: obtaining an intermediate map for that intermediate correlation by subtracting one of the analysis images corresponding to that intermediate correlation from the other analysis image corresponding to that intermediate correlation; dividing the intermediate map for that intermediate correlation into a plurality of units, wherein each unit is a matrix of values having dimensions at least as great as those of the point spread function; for each location in the point spread function, calculating a correlation between a first set of values and a second set of values, wherein: the first set of values comprises, for each unit from the plurality of units, a value at a first location in that unit; and the second set of values comprises, for each unit from the plurality of units, a value at a second location in that unit, wherein the first location for the value from that unit in the first set of values has a position relative to the second location that is the same as that location's position in the point spread function relative to the center of the point spread function; determining the set of noise dependencies based on the plurality of intermediate correlations.

An implementation relates to a bioassay system comprising a sensor array and means for generating a point spread function based on images captured using the sensor array during real time analysis of a biological sample.

While multiple examples are described, still other examples of the described subject matter will become apparent to those skilled in the art from the following detailed description and drawings, which show and describe illustrative examples of disclosed subject matter. As will be realized, the disclosed subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 10 illustrates how a first image may be subtracted from a second image to provide a noise map.

FIG. 16 illustrates four point spread functions.

DETAILED DESCRIPTION

Figure 1:
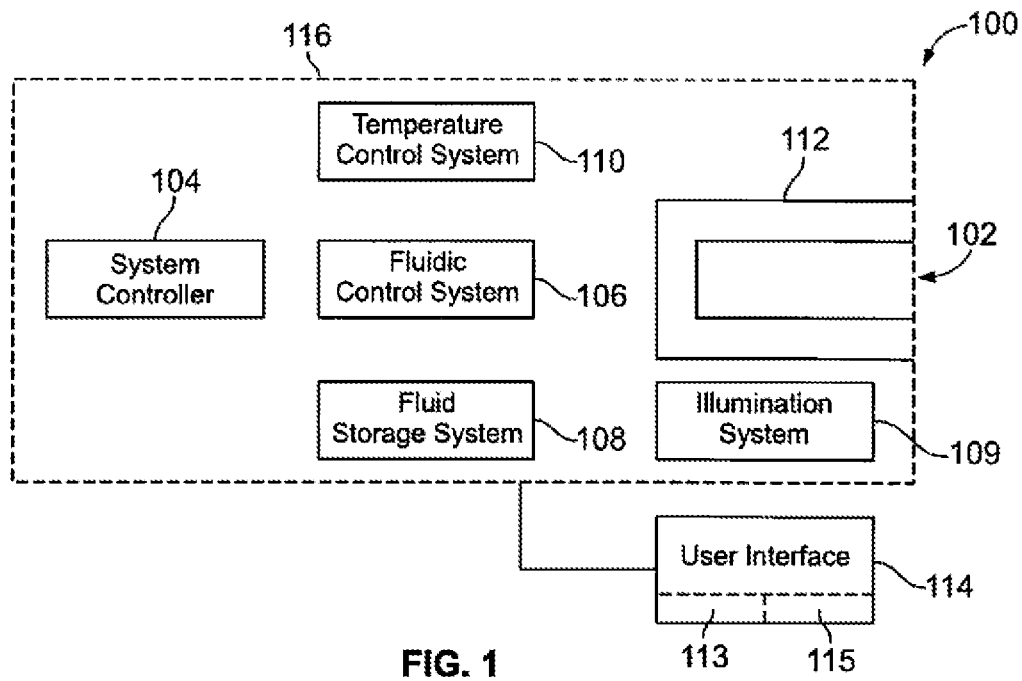
FIG. 1 is a block diagram of an exemplary system for biological or chemical analysis.

Examples described herein may be used in various biological or chemical processes and systems for academic or commercial analysis. More specifically, examples described herein may be used in various processes and systems where it is desired to detect an event, property, quality, or characteristic that is indicative of a designated reaction. For instance, examples described herein include cartridges, biosensors, and their components as well as bioassay systems that operate with cartridges and biosensors. In particular examples, the cartridges and biosensors include a flow cell and one or more light sensors that are coupled together in a substantially unitary structure.

The bioassay systems may be configured to perform a plurality of designated reactions that may be detected individually or collectively. The biosensors and bioassay systems may be configured to perform numerous cycles in which the plurality of designated reactions occurs in parallel. For example, the bioassay systems may be used to sequence a dense array of DNA features through iterative cycles of enzymatic manipulation and image acquisition. As such, the cartridges and biosensors may include one or more microfluidic channels that deliver reagents or other reaction components to a reaction site. In some examples, the reaction sites are randomly distributed across a substantially planer surface. For example, the reaction sites may have an uneven distribution in which some reaction sites are located closer to each other than other reaction sites. In other examples, the reaction sites are patterned across a substantially planer surface in a predetermined manner. Each of the reaction sites may be associated with one or more light sensors that detect light from the associated reaction site. Yet in other examples, the reaction sites are located in reaction chambers that compartmentalize the designated reactions therein.

The following detailed description of certain examples will be better understood when read in conjunction with the appended drawings. To the extent that the figures illustrate diagrams of the functional blocks of various examples, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various examples are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one example" are not intended to be interpreted as excluding the existence of additional examples that also incorporate the recited features. Moreover, unless explicitly stated to the contrary, examples "comprising" or "having" an element or a plurality of elements having a particular property may include additional elements whether or not they have that property.

As used herein, a "designated reaction" includes a change in at least one of a chemical, electrical, physical, or optical property (or quality) of an analyte-of-interest. In particular examples, the designated reaction is a positive binding event (e.g., incorporation of a fluorescently labeled biomolecule with the analyte-of-interest). More generally, the designated reaction may be a chemical transformation, chemical change, or chemical interaction. In particular examples, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a designated reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term "reaction site" is a localized region where a designated reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some examples a reaction site may contain only a single nucleic acid molecule, for example, in a single stranded or double stranded form. Furthermore, a plurality of reaction sites may be randomly distributed along the support surface or arranged in a predetermined manner (e.g., side-by-side in a matrix, such as in microarrays). A reaction site can also include a reaction chamber that at least partially defines a spatial region or volume configured to compartmentalize the designated reaction. As used herein, the term "reaction chamber" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some examples, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some examples, light sensors (e.g., photodiodes) are associated with corresponding reaction sites, and when light emitted from one reaction site is detected by a light sensor associated with another reaction site, this signal leakage may be treated as noise. A light sensor that is associated with a reaction site is configured to detect light emissions from the associated reaction site when a designated reaction has occurred at the associated reaction site. In some cases, a plurality of light sensors (e.g., several pixels of a camera device) may be associated with a single reaction site. In other cases, a single light sensor (e.g., a single pixel) may be associated with a single reaction site or with a group of reaction sites. The light sensor, the reaction site, and other features of the biosensor may be configured so that at least some of the light is directly detected by the light sensor without being reflected.

As used herein, the term "adjacent" when used with respect to two reaction sites means no other reaction site is located between the two reaction sites. The term "adjacent" may have a similar meaning when used with respect to adjacent detection paths and adjacent light sensors (e.g., adjacent light sensors have no other light sensor therebetween). In some cases, a reaction site may not be adjacent to another reaction site, but may still be within an immediate vicinity of the other reaction site. A first reaction site may be in the immediate vicinity of a second reaction site when fluorescent emission signals from the first reaction site are detected by the light sensor associated with the second reaction site. More specifically, a first reaction site may be in the immediate vicinity of a second reaction site when the light sensor associated with the second reaction site detects, for example, crosstalk from the first reaction site. Adjacent reaction sites can be contiguous such that they abut each other or the adjacent sites can be non-contiguous having an intervening space between.

As used herein, a "substance" includes items or solids, such as capture beads, as well as biological or chemical substances. As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species.

In a further example, a biological or chemical substance or a biomolecule includes an enzyme or reagent used in a coupled reaction to detect the product of another reaction such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated herein in its entirety.

Biomolecules, samples, and biological or chemical substances may be naturally occurring or synthetic and may be suspended in a solution or mixture within a spatial region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a structure having a plurality of reaction sites that is configured to detect designated reactions that occur at or proximate to the reaction sites. A biosensor may include a solid-state imaging device (e.g., CCD or CMOS imager) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver reactants to the reaction sites according to a predetermined protocol (e.g., sequencing-by-synthesis) and perform a plurality of imaging events. For example, the bioassay system may direct solutions to flow along the reaction sites. At least one of the solutions may include four types of nucleotides having the same or different fluorescent labels. The nucleotides may bind to corresponding oligonucleotides located at the reaction sites. The bioassay system may then illuminate the reaction sites using an excitation light source (e.g., solid-state light sources, such as light-emitting diodes or LEDs). The excitation light may have a predetermined wavelength or wavelengths, including a range of wavelengths. The excited fluorescent labels provide emission signals that may be detected by the light sensors.

As used herein, a "cartridge" includes a structure that is configured to hold a biosensor. In some examples, the cartridge may include additional features, such as the light source (e.g., LEDs) that are configured to provide excitation light to the reaction sites of the biosensor. The cartridge may also include a fluidic storage system (e.g., storage for reagents, sample, and buffer) and a fluidic control system (e.g., pumps, valves, and the like) for fluidically transporting reaction components, sample, and the like to the reaction sites. For example, after the biosensor is prepared or manufactured, the biosensor may be coupled to a housing or container of the cartridge. In some examples, the biosensors and the cartridges may be self-contained, disposable units. However, other examples may include an assembly with removable parts that allow a user to access an interior of the biosensor or cartridge for maintenance or replacement of components or samples. The biosensor and the cartridge may be removably coupled or engaged to larger bioassay systems, such as a sequencing system, that conducts controlled reactions therein.

As used herein, when the terms "removably" and "coupled" (or "engaged") are used together to describe a relationship between the biosensor (or cartridge) and a system receptacle or interface of a bioassay system, the term is intended to mean that a connection between the biosensor (or cartridge) and the system receptacle is readily separable without destroying or damaging the system receptacle and/or the biosensor (or cartridge). Components are readily separable when the components may be separated from each other without undue effort or a significant amount of time spent in separating the components. For example, the biosensor (or cartridge) may be removably coupled or engaged to the system receptacle in an electrical manner such that the mating contacts of the bioassay system are not destroyed or damaged. The biosensor (or cartridge) may also be removably coupled or engaged to the system receptacle in a mechanical manner such that the features that hold the biosensor (or cartridge) are not destroyed or damaged. The biosensor (or cartridge) may also be removably coupled or engaged to the system receptacle in a fluidic manner such that the ports of the system receptacle are not destroyed or damaged. The system receptacle or a component is not considered to be destroyed or damaged if, for example, only a simple adjustment to the component (e.g., realignment) or a simple replacement (e.g., replacing a nozzle) is required.

As used herein, the term "fluid communication" or "fluidically coupled" refers to two spatial regions being connected together such that a liquid or gas may flow between the two spatial regions. For example, a microfluidic channel may be in fluid communication with a reaction chamber such that a fluid may flow freely into the reaction chamber from the microfluidic channel. The terms "in fluid communication" or "fluidically coupled" allow for two spatial regions being in fluid communication through one or more valves, restrictors, or other fluidic components to control or regulate a flow of fluid through a system.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference in its entirety.

In some examples, nucleic acids can be attached to a surface and amplified using bridge amplification. Useful bridge amplification methods are described, for example, in U.S. Pat. No. 5,641,658; WO 07/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some examples, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any example, repeated rounds of extension (e.g., amplification) using the immobilized primer and primer in solution provide multiple copies of the nucleic acid.

In particular examples, the assay protocols executed by the systems and methods described herein include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In examples that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular examples, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example, in U.S. Patent Publ. Nos. 2008/0242560 A1 or 2008/0234136 A1, each of which is incorporated herein in its entirety. A substance that is held or disposed in a reaction chamber can be in a solid, liquid, or gaseous state.

FIG. 1 is a block diagram of a bioassay system 100 for biological or chemical analysis formed in accordance with one example. The term "bioassay" is not intended to be limiting as the bioassay system 100 may operate to obtain any information or data that relates to at least one of a biological or chemical substance. In some examples, the bioassay system 100 is a workstation that may be similar to a bench-top device or desktop computer. For example, a majority (or all) of the systems and components for conducting the designated reactions may be within a common housing 116.

In particular examples, the bioassay system 100 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some embodiments, the bioassay system 100 may also be configured to generate reaction sites in a biosensor. For example, the bioassay system 100 may be configured to receive a sample and generate surface attached clusters of clonally amplified nucleic acids derived from the sample. Each cluster may constitute or be part of a reaction site in the biosensor.

The exemplary bioassay system 100 may include a system receptacle or interface 112 that is configured to interact with a biosensor 102 to perform designated reactions within the biosensor 102. In the following description with respect to FIG. 1, the biosensor 102 is loaded into the system receptacle 112. However, it is understood that a cartridge that includes the biosensor 102 may be inserted into the system receptacle 112 and in some states the cartridge may be removed temporarily or permanently. As described above, the cartridge may include, among other things, fluidic control and fluidic storage components.

In particular examples, the bioassay system 100 is to perform a large number of parallel reactions within the biosensor 102. The biosensor 102 includes one or more reaction sites where designated reactions may occur. The reaction sites may be, for example, immobilized to a solid surface of the biosensor or immobilized to beads (or other movable substrates) that are located within corresponding reaction chambers of the biosensor. The reaction sites may include, for example, clusters of clonally amplified nucleic acids. The biosensor 102 may include a solid-state imaging device (e.g., CCD or CMOS imager) and a flow cell mounted thereto. The flow cell may include one or more flow channels that receive a solution from the bioassay system 100 and direct the solution toward the reaction sites. Optionally, the biosensor 102 may engage a thermal element for transferring thermal energy into or out of the flow channel.

The bioassay system 100 may include various components, assemblies, and systems (or sub-systems) that interact with each other to perform a predetermined method or assay protocol for biological or chemical analysis. For example, the bioassay system 100 includes a system controller 104 that may communicate with the various components, assemblies, and sub-systems of the bioassay system 100 and also the biosensor 102. For example, in addition to the system receptacle 112, the bioassay system 100 may also include a fluidic control system 106 to control the flow of fluid throughout a fluid network of the bioassay system 100 and the biosensor 102; a fluid storage system 108 that is to hold all fluids (e.g., gas or liquids) that may be used by the bioassay system; a temperature control system 110 that may regulate the temperature of the fluid in the fluid network, the fluid storage system 108, and/or the biosensor 102; and an illumination system 111 that is to illuminate the biosensor 102. As described above, if a cartridge having the biosensor 102 is loaded into the system receptacle 112, the cartridge may also include fluidic control and fluidic storage components.

Also shown, the bioassay system 100 may include a user interface 114 that interacts with the user. For example, the user interface 114 may include a display 113 to display or request information from a user and a user input device 115 to receive user inputs. In some examples, the display 113 and the user input device 115 are the same device. For example, the user interface 114 may include a touch-sensitive display to detect the presence of an individual's touch and also identify a location of the touch on the display. However, other user input devices 115 may be used, such as a mouse, touchpad, keyboard, keypad, handheld scanner, voice-recognition system, motion-recognition system, and the like. As will be discussed in greater detail below, the bioassay system 100 may communicate with various components, including the biosensor 102 (e.g., in the form of a cartridge), to perform the designated reactions. The bioassay system 100 may also analyze data obtained from the biosensor to provide a user with desired information. The system controller 104 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are not intended to limit in any way the definition and/or meaning of the term system controller. In an example, the system controller 104 executes a set of instructions that are stored in one or more storage elements, memories, or modules in order to at least one of obtain and analyze detection data. Storage elements may be in the form of information sources or physical memory elements within the bioassay system 100.

The set of instructions may include various commands that instruct the bioassay system 100 or biosensor 102 to perform specific operations such as the methods and processes of the various examples described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the bioassay system 100, processed in response to user inputs, or processed in response to a request made by another processing machine (e.g., a remote request through a communication link).

The system controller 104 may be connected to the biosensor 102 and the other components of the bioassay system 100 via communication links. The system controller 104 may also be communicatively connected to off-site systems or servers. The communication links may be hard-wired or wireless. The system controller 104 may receive user inputs or commands, from the user interface 114 and the user input device 115.

The fluidic control system 106 includes a fluid network and is to direct and regulate the flow of one or more fluids through the fluid network. The fluid network may be in fluid communication with the biosensor 102 and the fluid storage system 108. For example, select fluids may be drawn from the fluid storage system 108 and directed to the biosensor 102 in a controlled manner, or the fluids may be drawn from the biosensor 102 and directed toward, for example, a waste reservoir in the fluid storage system 108. Although not shown, the fluidic control system 106 may include flow sensors that detect a flow rate or pressure of the fluids within the fluid network. The sensors may communicate with the system controller 104.

The temperature control system 110 is to regulate the temperature of fluids at different regions of the fluid network, the fluid storage system 108, and/or the biosensor 102. For example, the temperature control system 110 may include a thermocycler that interfaces with the biosensor 102 and controls the temperature of the fluid that flows along the reaction sites in the biosensor 102. The temperature control system 110 may also regulate the temperature of solid elements or components of the bioassay system 100 or the biosensor 102. Although not shown, the temperature control system 110 may include sensors to detect the temperature of the fluid or other components. The sensors may communicate with the system controller 104.

The fluid storage system 108 is in fluid communication with the biosensor 102 and may store various reaction components or reactants that are used to conduct the designated reactions therein. The fluid storage system 108 may also store fluids for washing or cleaning the fluid network and biosensor 102 and for diluting the reactants. For example, the fluid storage system 108 may include various reservoirs to store samples, reagents, enzymes, other biomolecules, buffer solutions, aqueous, and non-polar solutions, and the like. Furthermore, the fluid storage system 108 may also include waste reservoirs for receiving waste products from the biosensor 102. In examples that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 111 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In embodiments that use an illumination system, the illumination system 111 may be configured to direct an excitation light to reaction sites. As one example, fluorophores may be excited by green wavelengths of light, as such the wavelength of the excitation light may be approximately 532 nm.

The system receptacle or interface 112 is to engage the biosensor 102 in at least one of a mechanical, electrical, and fluidic manner. The system receptacle 112 may hold the biosensor 102 in a desired orientation to facilitate the flow of fluid through the biosensor 102. The system receptacle 112 may also include electrical contacts that are to engage the biosensor 102 so that the bioassay system 100 may communicate with the biosensor 102 and/or provide power to the biosensor 102. Furthermore, the system receptacle 112 may include fluidic ports (e.g., nozzles) that are to engage the biosensor 102. In some examples, the biosensor 102 is removably coupled to the system receptacle 112 in a mechanical manner, in an electrical manner, and also in a fluidic manner.

In addition, the bioassay system 100 may communicate remotely with other systems or networks or with other bioassay systems 100. Detection data obtained by the bioassay system(s) 100 may be stored in a remote database.

Figure 2:
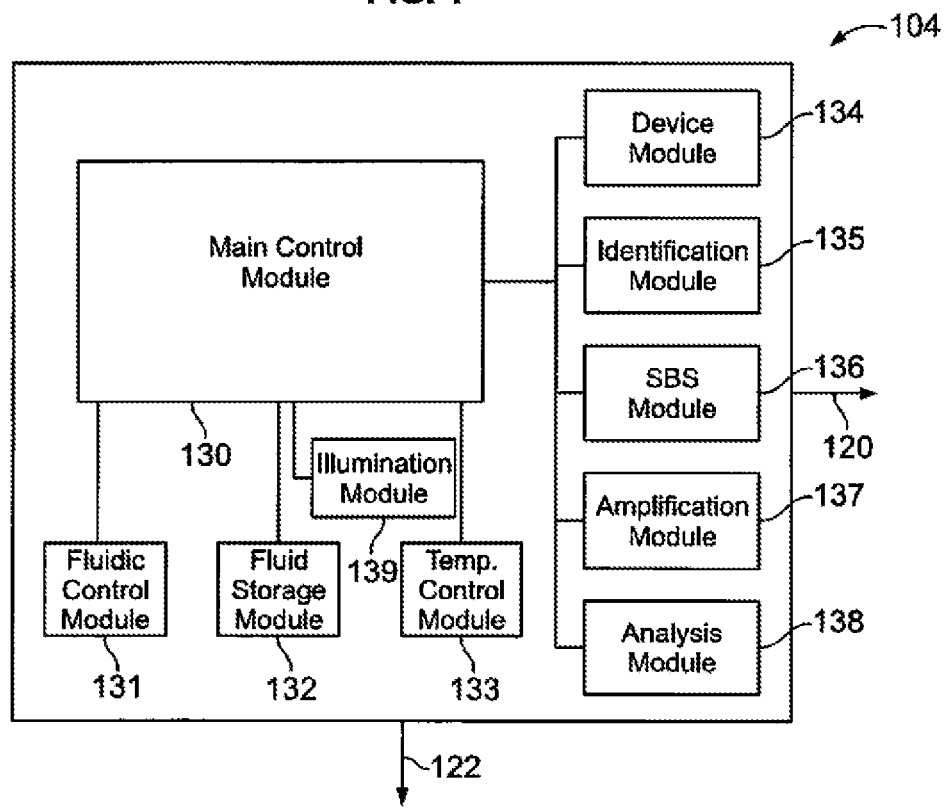
FIG. 2 is a block diagram of an exemplary system controller that may be used in the system of FIG. 1.

FIG. 2 is a block diagram of the system controller 104 in an example. In one example, the system controller 104 includes one or more processors or modules that may communicate with one another. Each of the processors or modules may include an algorithm (e.g., instructions stored on a tangible and/or non-transitory computer readable storage medium) or sub-algorithms to perform particular processes. The system controller 104 is illustrated conceptually as a collection of modules, but may be implemented utilizing any combination of dedicated hardware boards, DSPs, processors, etc. Alternatively, the system controller 104 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication link 120 may transmit information (e.g., commands) to or receive information (e.g., data) from the biosensor 102 (FIG. 1) and/or the sub-systems 106, 108, 110 (FIG. 1). A communication link 122 may receive user input from the user interface 114 (FIG. 1) and transmit data or information to the user interface 114. Data from the biosensor 102 or sub-systems 106, 108, 110 may be processed by the system controller 104 in real-time during a bioassay session. Additionally or alternatively, data may be stored temporarily in a system memory during a bioassay session and processed in slower than real-time or off-line operation.

As shown in FIG. 2, the system controller 104 may include a plurality of modules 131-139 that communicate with a main control module 130. The main control module 130 may communicate with the user interface 114 (FIG. 1). Although the modules 131-139 are shown as communicating directly with the main control module 130, the modules 131-139 may also communicate directly with each other, the user interface 114, and the biosensor 102. Also, the modules 131-139 may communicate with the main control module 130 through the other modules.

The plurality of modules 131-139 include system modules 131-133, 139 that communicate with the sub-systems 106, 108, 110, and 111, respectively. The fluidic control module 131 may communicate with the fluidic control system 106 to control the valves and flow sensors of the fluid network for controlling the flow of one or more fluids through the fluid network. The fluid storage module 132 may notify the user when fluids are low or when the waste reservoir is at or near capacity. The fluid storage module 132 may also communicate with the temperature control module 133 so that the fluids may be stored at a desired temperature. The illumination module 139 may communicate with the illumination system 109 to illuminate the reaction sites at designated times during a protocol, such as after the designated reactions (e.g., binding events) have occurred.

The plurality of modules 131-139 may also include a device module 134 that communicates with the biosensor 102 and an identification module 135 that determines identification information relating to the biosensor 102. The device module 134 may, for example, communicate with the system receptacle 112 to confirm that the biosensor has established an electrical and fluidic connection with the bioassay system 100. The identification module 135 may receive signals that identify the biosensor 102. The identification module 135 may use the identity of the biosensor 102 to provide other information to the user. For example, the identification module 135 may determine and then display a lot number, a date of manufacture, or a protocol that is recommended to be run with the biosensor 102.

The plurality of modules 131-139 may also include a detection data analysis module 138 that receives and analyzes the signal data (e.g., image data) from the biosensor 102. The signal data may be stored for subsequent analysis or may be transmitted to the user interface 114 to display desired information to the user. In some embodiments, the signal data may be processed by the solid-state imager (e.g., CMOS image sensor) before the detection data analysis module 138 receives the signal data.

Protocol modules 136 and 137 communicate with the main control module 130 to control the operation of the sub-systems 106, 108, and 110 when conducting predetermined assay protocols. The protocol modules 136 and 137 may include sets of instructions for instructing the bioassay system 100 to perform specific operations pursuant to predetermined protocols. As shown, the protocol module may be a sequencing-by-synthesis (SBS) module 136 that is configured to issue various commands for performing sequencing-by-synthesis processes. In SBS, extension of a nucleic acid primer along a nucleic acid template is monitored to determine the sequence of nucleotides in the template. The underlying chemical process may be polymerization (e.g., as catalyzed by a polymerase enzyme) or ligation (e.g., catalyzed by a ligase enzyme). In a particular polymerase-based SBS example, fluorescently labeled nucleotides are added to a primer (thereby extending the primer) in a template dependent fashion such that detection of the order and type of nucleotides added to the primer may be used to determine the sequence of the template. For example, to initiate a first SBS cycle, commands may be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated may be detected through an imaging event. During an imaging event, the illumination system 111 may provide an excitation light to the reaction sites. Optionally, the nucleotides may further include a reversible termination property that terminates further primer extension once a nucleotide has been added to a primer. For example, a nucleotide analog having a reversible terminator moiety may be added to a primer such that subsequent extension cannot occur until a deblocking agent is delivered to remove the moiety. Thus, for examples that use reversible termination a command may be given to deliver a deblocking reagent to the flow cell (before or after detection occurs). One or more commands may be given to effect wash(es) between the various delivery steps. The cycle may then be repeated n times to extend the primer by n nucleotides, thereby detecting a sequence of length n. Exemplary sequencing techniques are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

For the nucleotide delivery step of an SBS cycle, either a single type of nucleotide may be delivered at a time, or multiple different nucleotide types (e.g. A, C, T and G together) may be delivered. For a nucleotide delivery configuration where only a single type of nucleotide is present at a time, the different nucleotides need not have distinct labels since they may be distinguished based on temporal separation inherent in the individualized delivery. Accordingly, a sequencing method or apparatus may use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types may be distinguished based on different fluorescent labels that are attached to respective nucleotide types in the mixture. For example, four different nucleotides may be used, each having one of four different fluorophores. In one embodiment, the four different fluorophores may be distinguished using excitation in four different regions of the spectrum. For example, four different excitation radiation sources may be used. Alternatively, fewer than four different excitation sources may be used, but optical filtration of the excitation radiation from a single source may be used to produce different ranges of excitation radiation at the flow cell.

In some examples, fewer than four different colors may be detected in a mixture having four different nucleotides. For example, pairs of nucleotides may be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. No. 61/538,294 and 61/619,878, which are incorporated herein by reference their entireties. U.S. application Ser. No. 13/624,200, which was filed on Sep. 21, 2012, is also incorporated by reference in its entirety.

The plurality of protocol modules may also include a sample-preparation (or generation) module 137 that is to issue commands to the fluidic control system 106 and the temperature control system 110 for amplifying a product within the biosensor 102. For example, the biosensor 102 may be engaged to the bioassay system 100. The amplification module 137 may issue instructions to the fluidic control system 106 to deliver necessary amplification components to reaction chambers within the biosensor 102. In other embodiments, the reaction sites may already contain some components for amplification, such as the template DNA and/or primers. After delivering the amplification components to the reaction chambers, the amplification module 137 may instruct the temperature control system 110 to cycle through different temperature stages according to known amplification protocols. In some examples, the amplification and/or nucleotide incorporation is performed isothermally.

The SBS module 136 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method may be used as set forth above or as follows.

Each sequencing cycle may extend a sstDNA by a single base which may be accomplished for example by using a modified DNA polymerase and a mixture of four types of nucleotides. The different types of nucleotides may have unique fluorescent labels, and each nucleotide may further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar sequencing cycle may follow. In such a sequencing protocol, the SBS module 136 may instruct the fluidic control system 106 to direct a flow of reagent and enzyme solutions through the biosensor 102. Exemplary reversible terminator-based SBS methods which may be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/0281109 A1, PCT Publication No. WO 05/065814, US Patent Application Publication No. 2005/0100900 A1, PCT Publication No. WO 06/064199 and PCT Publication No. WO 07/010251, each of which is incorporated herein by reference in its entirety. Exemplary reagents for reversible terminator-based SBS are described in U.S. Pat. Nos. 7,541,444; 7,057,026; 7,414,116; 7,427,673; 7,566,537; 7,592,435 and WO 07/135368, each of which is incorporated herein by reference in its entirety.

In some examples, the amplification and SBS modules may operate in a single assay protocol where, for example, template nucleic acid is amplified and subsequently sequenced within the same cartridge.

The bioassay system 100 may also allow the user to reconfigure an assay protocol. For example, the bioassay system 100 may offer options to the user through the user interface 114 for modifying the determined protocol. For example, if it is determined that the biosensor 102 is to be used for amplification, the bioassay system 100 may request a temperature for the annealing cycle. Furthermore, the bioassay system 100 may issue warnings to a user if a user has provided user inputs that are generally not acceptable for the selected assay protocol.

Figure 3:
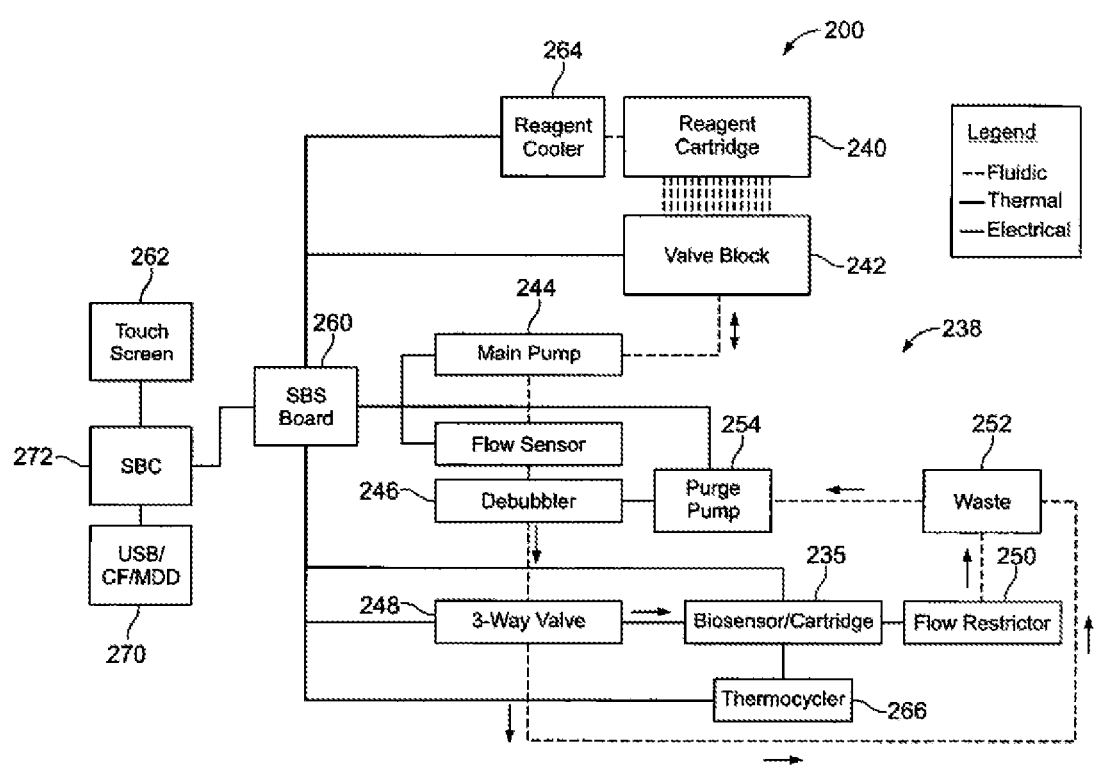
FIG. 3 is a block diagram of an exemplary workstation for biological or chemical analysis.

FIG. 3 is a block diagram of an exemplary workstation 200 for biological or chemical analysis in accordance with one example. The workstation 200 may have similar features, systems, and assemblies as the bioassay system 100 described above. For example, the workstation 200 may have a fluidic control system, such as the fluidic control system 106 (FIG. 1), that is fluidicly coupled to a biosensor (or cartridge) 235 through a fluid network 238. The fluid network 238 may include a reagent cartridge 240, a valve block 242, a main pump 244, a debubbler 246, a 3-way valve 248, a flow restrictor 250, a waste removal system 252, and a purge pump 254. In particular examples, most of the components or all of the components described above are within a common workstation housing (not shown). Although not shown, the workstation 200 may also include an illumination system, such as the illumination system 111, that is to provide an excitation light to the reaction sites.

A flow of fluid is indicated by arrows along the fluid network 238. For example, reagent solutions may be removed from the reagent cartridge 240 and flow through the valve block 242. The valve block 242 may facilitate creating a zero-dead volume of the fluid flowing to the cartridge 235 from the reagent cartridge 240. The valve block 242 may select or permit one or more liquids within the reagent cartridge 240 to flow through the fluid network 238. For example, the valve block 242 may include solenoid valves that have a compact arrangement. Each solenoid valve may control the flow of a fluid from a single reservoir bag. In some examples, the valve block 242 can permit two or more different liquids to flow into the fluid network 238 at the same time thereby mixing the two or more different liquids. After leaving the valve block 242, the fluid may flow through the main pump 244 and to the debubbler 246. The debubbler 246 is to remove unwanted gases that have entered or been generated within the fluid network 238.

From the debubbler 246, fluid may flow to the 3-way valve 248 where the fluid is either directed to the cartridge 235 or bypassed to the waste removal system 252. A flow of the fluid within the cartridge 235 may be at least partially controlled by the flow restrictor 250 located downstream from the cartridge 235. Furthermore, the flow restrictor 250 and the main pump 244 may coordinate with each other to control the flow of fluid across reaction sites and/or control the pressure within the fluid network 238. Fluid may flow through the cartridge 235 and onto the waste removal system 252. Optionally, fluid may flow through the purge pump 254 and into, for example, a waste reservoir bag within the reagent cartridge 240.

Also shown in FIG. 3, the workstation 200 may include a temperature control system, such as the temperature control system 110, that is to regulate or control a thermal environment of the different components and sub-systems of the workstation 200. The temperature control system 110 may include a reagent cooler 264 that is to control the temperature requirements of various fluids used by the workstation 200, and a thermocycler 266 that is to control the temperature of a cartridge 235. The thermocycler 266 may include a thermal element (not shown) that interfaces with the cartridge.

Furthermore, the workstation 200 may include a system controller or SBS board 260 that may have similar features as the system controller 104 described above. The SBS board 260 may communicate with the various components and sub-systems of the workstation 200 as well as the cartridge 235. Furthermore, the SBS board 260 may communicate with remote systems to, for example, store data or receive commands from the remote systems. The workstation 200 may also include a touch screen user interface 262 that is operatively coupled to the SBS board 260 through a single-board computer (SBC) 272. The workstation 200 may also include one or more user accessible data communication ports and/or drives. For example, a workstation 200 may include one or more universal serial bus (USB) connections for computer peripherals, such as a flash or jump drive, a compact-flash (CF) drive and/or a hard drive 270 for storing user data in addition to other software.

Figure 4:
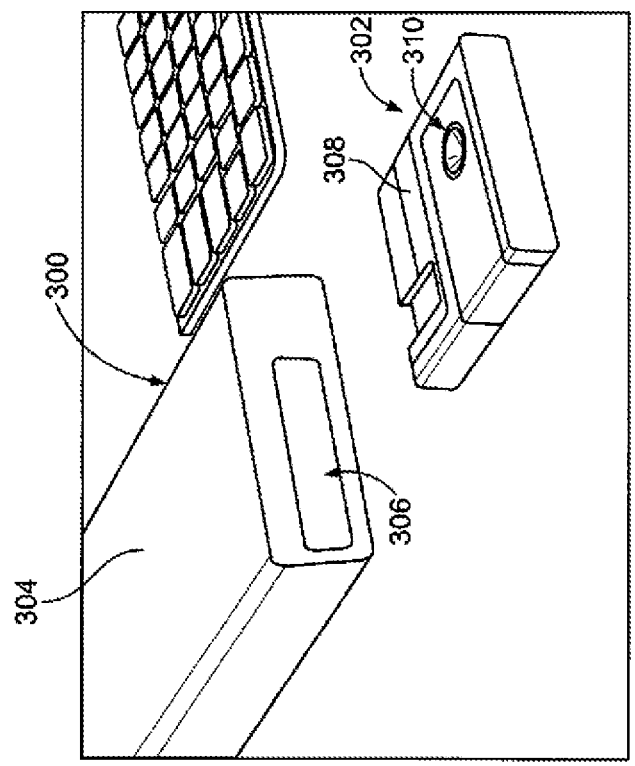
FIG. 4 is a perspective view of an exemplary workstation and an exemplary cartridge.

FIG. 4 is a perspective view of a workstation 300 and a cartridge 302 that may include one or more biosensors (not shown) as described herein. The workstation 300 may include similar components as described above with respect to the bioassay system 100 and the workstation 200 and may operate in a similar manner. For example, the workstation 300 may include a workstation housing 304 and a system receptacle 306 that is to receive and engage the cartridge 302. The system receptacle may at least one of fluidically or electrically engage the cartridge 302. The workstation housing 304 may hold, for example, a system controller, a fluid storage system, a fluidic control system, and a temperature control system as described above. In FIG. 4, the workstation 300 does not include a user interface or display that is coupled to the workstation housing 304. However, a user interface may be communicatively coupled to the housing 304 (and the components/systems therein) through a communication link. Thus, the user interface and the workstation 300 may be remotely located with respect to each other. Together, the user interface and the workstation 300 (or a plurality of workstations) may constitute a bioassay system.

As shown, the cartridge 302 includes a cartridge housing 308 having at least one port 310 that provides access to an interior of the cartridge housing 308. For example, a solution that is to be used in the cartridge 302 during the controlled reactions may be inserted through the port 310 by a technician or by the workstation 300. The system receptacle 306 and the cartridge 302 may be sized and shaped relative to each other such that the cartridge 302 may be inserted into a receptacle cavity (not shown) of the system receptacle 306.

Figure 5:
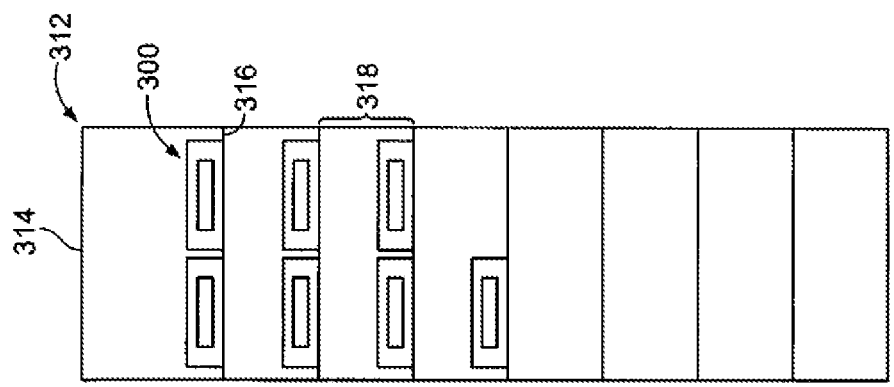
FIG. 5 is a front view of an exemplary rack assembly that includes a plurality of the workstations of FIG. 4.

FIG. 5 is a front view of a rack assembly 312 having a cabinet or carriage 314 with a plurality of the workstations 300 loaded thereon. The cabinet 314 may include one or more shelves 316 that define one or more reception spaces 318 to receive one or more workstations 300. Although not shown, the workstations 300 may be communicatively coupled to a communication network that permits a user to control operation of the workstations 300. In some examples, a bioassay system includes a plurality of workstations, such as the workstations 300, and a single user interface to control operation of the multiple workstations.

Figure 6:
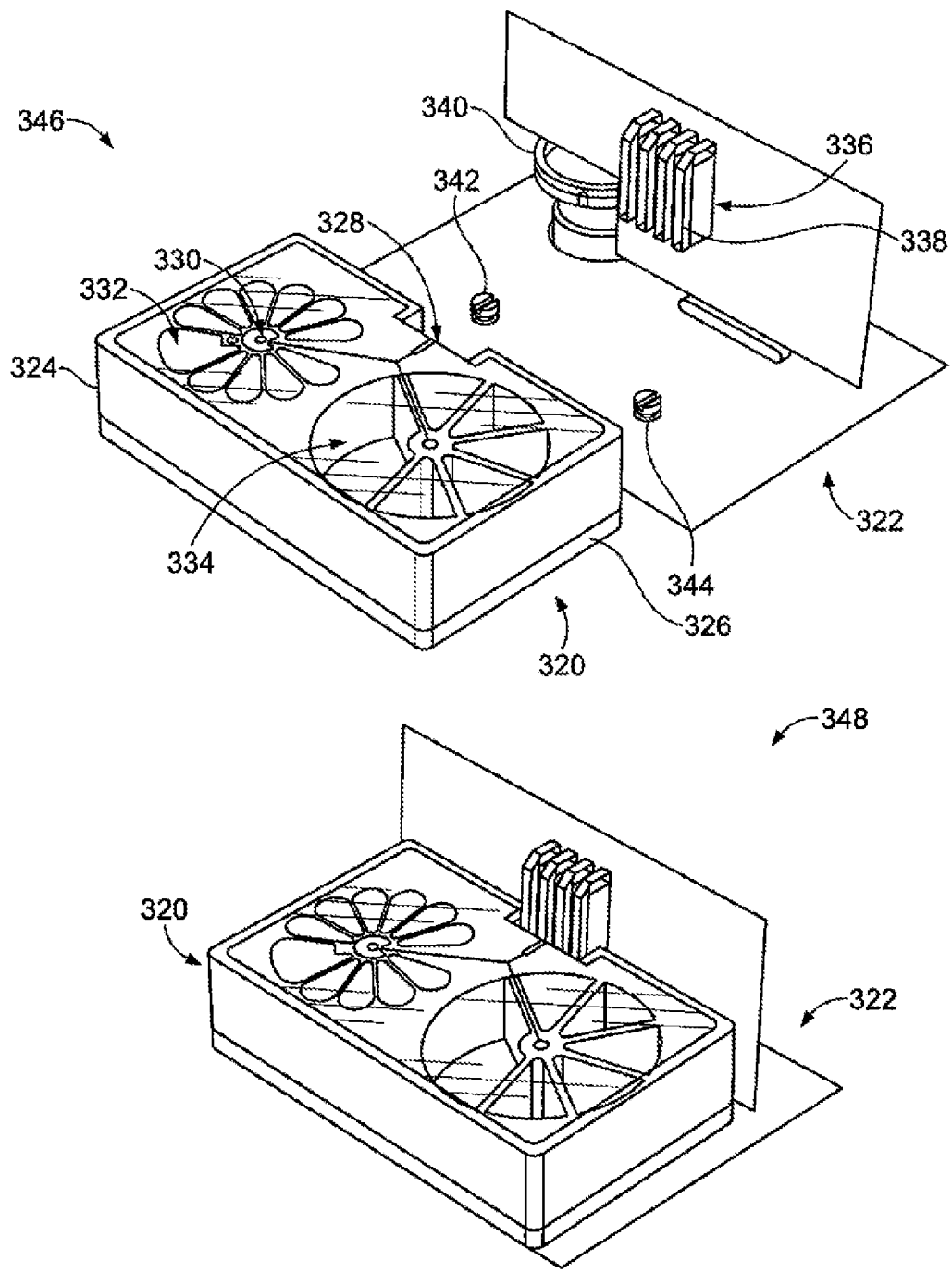
FIG. 6 illustrates internal components of an exemplary cartridge.

FIG. 6 illustrates various features of the cartridge 302 (FIG. 4) in accordance with one example. As shown, the cartridge 302 may include a sample assembly 320, and the system receptacle 306 may include a light assembly 322. Stage 346 shown in FIG. 6 represents the spatial relationship between the first and second sub-assemblies 320 and 322 when they are separate from each other. At stage 348, the first and second sub-assemblies 320 and 322 are joined together. The cartridge housing 308 (FIG. 4) may enclose the joined first and second sub-assemblies 320 and 322.

In the illustrated example, the first sub-assembly 320 includes a base 326 and a reaction-component body 324 that is mounted onto the base 326. Although not shown, one or more biosensors may be mounted to the base 326 in a recess 328 that is defined, at least in part, by the reaction-component body 324 and the base 326. For example, at least four biosensors may be mounted to the base 326. In some examples, the base 326 is a printed circuit board having circuitry that enables communication between the different components of the cartridge and the workstation 300 (FIG. 4). For example, the reaction-component body 324 may include a rotary valve 330 and reagent reservoirs 332 that are fluidically coupled to the rotary valve 330. The reaction-component body 324 may also include additional reservoirs 334.

The second sub-assembly 322 includes a light assembly 336 that includes a plurality of light directing channels 338. Each light directing channel 338 is optically coupled to a light source (not shown), such as a light-emitting diode (LED). The light source(s) are to provide an excitation light that is directed by the light directing channels 338 onto the biosensors. In alternative examples, the cartridge may not include a light source(s). In such examples, the light source (s) may be located in the workstation 300. When the cartridge is inserted into the system receptacle 306 (FIG. 4), the cartridge 302 may align with the light source(s) so that the biosensors may be illuminated.

Also shown in FIG. 6, the second sub-assembly 322 includes a cartridge pump 340 that is fluidically coupled to ports 342 and 344. When the first and second sub-assemblies 320 and 322 are joined together, the port 342 is coupled to the rotary valve 330 and the port 344 is coupled to the other reservoirs 334. The cartridge pump 340 may be activated to direct reaction components from the reservoirs 332 and/or 334 to the biosensors according to a designated protocol.

Figure 7:
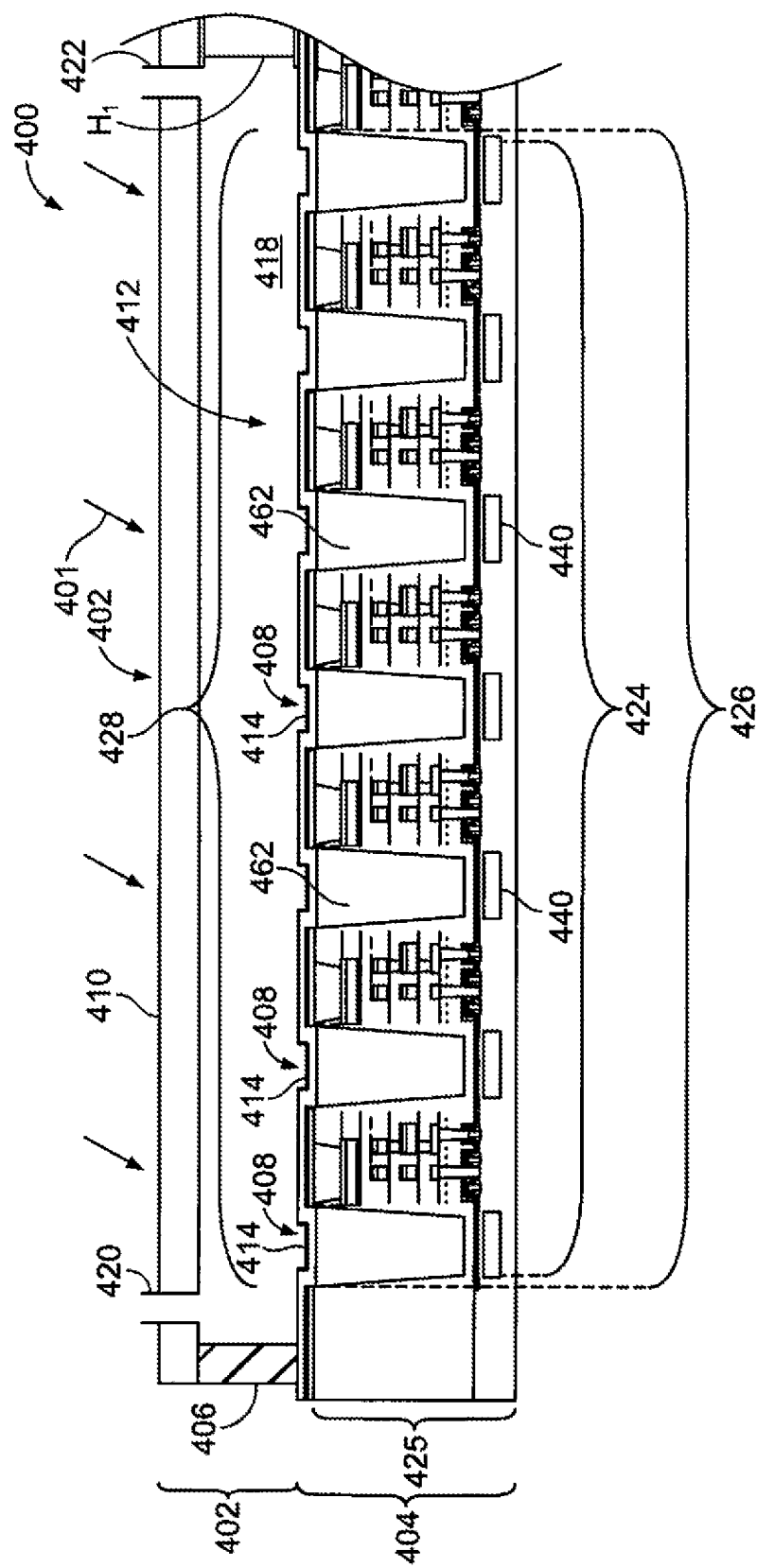
FIG. 7 illustrates a cross-section of a biosensor.

FIG. 7 illustrates a cross-section of a portion of an exemplary biosensor 400 formed in accordance with one example. The biosensor 400 may include similar features as the biosensor 102 (FIG. 1) described above and may be used in, for example, the cartridge 302 (FIG. 4). As shown, the biosensor 400 may include a flow cell 402 that is coupled directly or indirectly to a detection device 404. The flow cell 402 may be mounted to the detection device 404. In the illustrated embodiment, the flow cell 402 is affixed directly to the detection device 404 through one or more securing mechanisms (e.g., adhesive, bond, fasteners, and the like). In some examples, the flow cell 402 may be removably coupled to the detection device 404.

In the illustrated example, the detection device 404 includes a device base 425. In particular examples, the device base 425 includes a plurality of stacked layers (e.g., silicon layer, dielectric layer, metal-dielectric layers, etc.). The device base 425 may include a sensor array 424 of light sensors 440, a guide array 426 of light guides 462, and a reaction array 428 of reaction recesses 408 that have corresponding reaction sites 414. In certain examples, the components are arranged such that each light sensor 440 aligns with a single light guide 462 and a single reaction site 414. However, in other examples, a single light sensor 440 may receive photons through more than one light guide 462 and/or from more than one reaction site 414. As used herein, a single light sensor may include one pixel or more than one pixel.

Moreover, it is noted that the term "array" or "sub-array" does not necessarily include each and every item of a certain type that the detection device may have. For example, the sensor array 424 may not include each and every light sensor in the detection device 404. Instead, the detection device 404 may include other light sensors (e.g., other array(s) of light sensors). As another example, the guide array 426 may not include each and every light guide of the detection device. Instead, there may be other light guides that are configured differently than the light guides 462 or that have different relationships with other elements of the detection device 404. As such, unless explicitly recited otherwise, the term "array" may or may not include all such items of the detection device.

In the illustrated example, the flow cell 402 includes a sidewall 406 and a flow cover 410 that is supported by the sidewall 406 and other sidewalls (not shown). The sidewalls are coupled to the detector surface 412 and extend between the flow cover 410 and the detector surface 412. In some examples, the sidewalls are formed from a curable adhesive layer that bonds the flow cover 410 to the detection device 404.

The flow cell 402 is sized and shaped so that a flow channel 418 exists between the flow cover 410 and the detection device 404. As shown, the flow channel 418 may include a height $H_1$. By way of example only, the height $H_1$ may be between about 50-400 µm (microns) or, more particularly, about 80-200 µm. In the illustrated example, the height $H_1$ is about 100 µm. The flow cover 410 may include a material that is transparent to excitation light 401 propagating from an exterior of the biosensor 400 into the flow channel 418. As shown in FIG. 7, the excitation light 401 approaches the flow cover 410 at a non-orthogonal angle. However, this is only for illustrative purposes as the excitation light 401 may approach the flow cover 410 from different angles.

Also shown, the flow cover 410 may include inlet and outlet ports 420, 422 that are to fluidically engage other ports (not shown). For example, the other ports may be from the cartridge 302 (FIG. 4) or the workstation 300 (FIG. 4). The flow channel 418 is sized and shaped to direct a fluid along the detector surface 412. The height $H_1$ and other dimensions of the flow channel 418 may be to maintain a substantially even flow of a fluid along the detector surface 412. The dimensions of the flow channel 418 may also be to control bubble formation.

The sidewalls 406 and the flow cover 410 may be separate components that are coupled to each other. In other examples, the sidewalls 406 and the flow cover 410 may be integrally formed such that the sidewalls 406 and the flow cover 410 are formed from a continuous piece of material. By way of example, the flow cover 410 (or the flow cell 402) may comprise a transparent material, such as glass or plastic. The flow cover 410 may constitute a substantially rectangular block having a planar exterior surface and a planar inner surface that defines the flow channel 418. The block may be mounted onto the sidewalls 406. Alternatively, the flow cell 402 may be etched to define the flow cover 410 and the sidewalls 406. For example, a recess may be etched into the transparent material. When the etched material is mounted to the detection device 404, the recess may become the flow channel 418.

The detection device 404 has a detector surface 412 that may be functionalized (e.g., chemically or physically modified in a suitable manner for conducting designated reactions). For example, the detector surface 412 may be functionalized and may include a plurality of reaction sites 414 having one or more biomolecules immobilized thereto. The detector surface 412 has an array of reaction recesses or open-sided reaction chambers 408. Each of the reaction recesses 408 may include one or more of the reaction sites 414. The reaction recesses 408 may be defined by, for example, an indent or change in depth along the detector surface 412. In other examples, the detector surface 412 may be substantially planar.

As shown in FIG. 7, the reaction sites 414 may be distributed in a pattern along the detector surface 412. For instance, the reactions sites 414 may be located in rows and columns along the detector surface 412 in a manner that is similar to a microarray. However, it is understood that various patterns of reaction sites may be used. The reaction sites may include biological or chemical substances that emit light signals. For example, the biological or chemical substances of the reaction sites may generate light emissions in response to the excitation light 401. In particular examples, the reaction sites 414 include clusters or colonies of biomolecules (e.g., oligonucleotides) that are immobilized on the detector surface 412.

Figure 8:
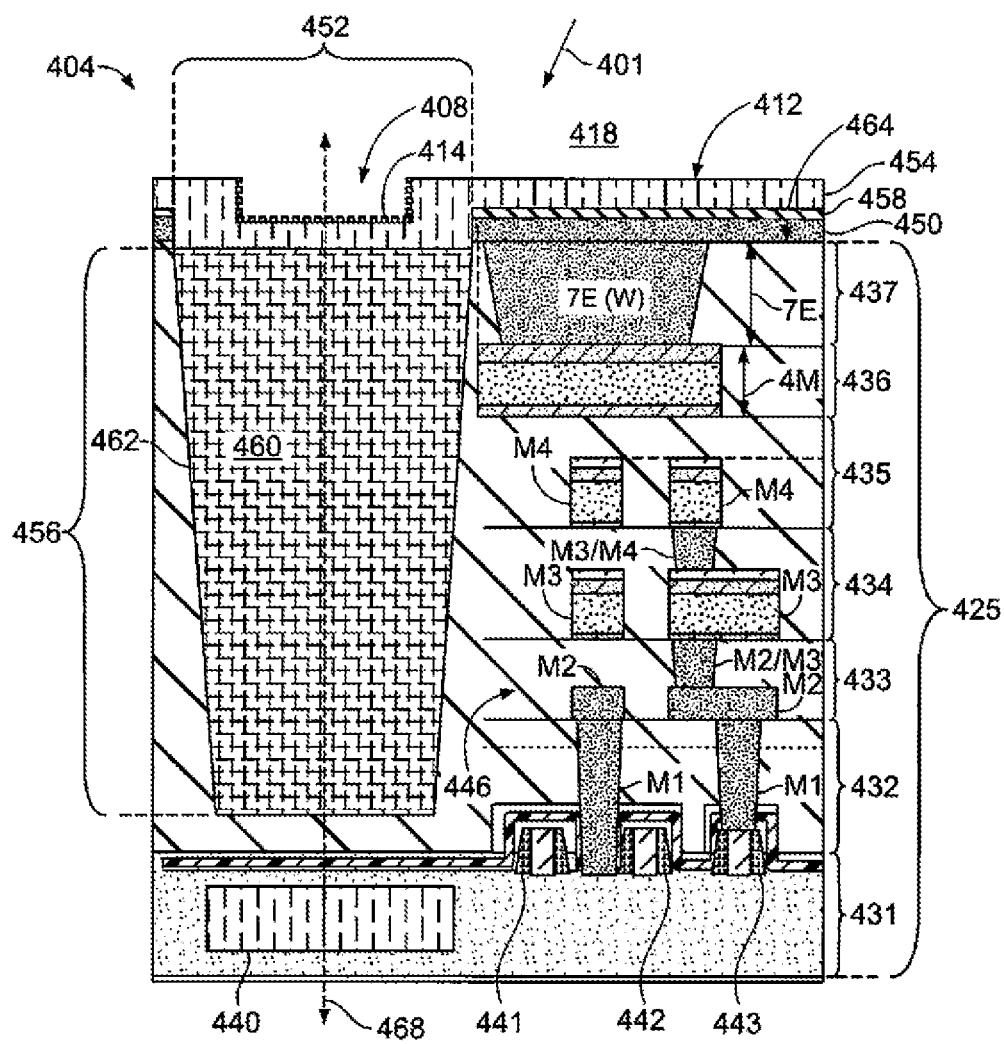
FIG. 8 is an enlarged portion of the cross-section of FIG. 7 illustrating the biosensor in greater detail.

FIG. 8 is an enlarged cross-section of the detection device 404 showing various features in greater detail. More specifically, FIG. 8 shows a single light sensor 440, a single light guide 462 for directing light emissions toward the light sensor 440, and associated circuitry 446 for transmitting signals based on the light emissions (e.g., photons) detected by the light sensor 440. It is understood that the other light sensors 440 of the sensor array 424 (FIG. 7) and associated components may be configured in an identical or similar manner. It is also understood, however, the detection device 404 is not required to be manufactured identically or uniformly throughout. Instead, one or more light sensors 440 and/or associated components may be manufactured differently or have different relationships with respect to one another.

The circuitry 446 may include interconnected conductive elements (e.g., conductors, traces, vias, interconnects, etc.) that are capable of conducting electrical current, such as the transmission of data signals that are based on detected photons. In some examples, the circuitry 446 may be similar to or include a microcircuit arrangement, such as the microcircuit arrangement described in U.S. Pat. No. 7,595,883, which is incorporated herein by reference in the entirety. The detection device 404 and/or the device base 425 may comprise an integrated circuit having a planar array of the light sensors 440. The circuitry 446 formed within the detection device 425 may be for at least one of signal amplification, digitization, storage, and processing. The circuitry may collect and analyze the detected light emissions and generate data signals for communicating detection data to a bioassay system. The circuitry 446 may also perform additional analog and/or digital signal processing in the detection device 404.

The device base 425 may be manufactured using integrated circuit manufacturing processes, such as processes used to manufacture complementary-metal-oxide semiconductors (CMOSs). For example, the device base 425 may include a plurality of stacked layers 431-437 including a sensor layer or base 431, which is a silicon layer or wafer in the illustrated example. The sensor layer 431 may include the light sensor 440 and gates 441-443 that are formed with the sensor layer 431. The gates 441-443 are electrically coupled to the light sensor 440. When the detection device 404 is fully formed as shown in FIGS. 7 and 8, the light sensor 440 may be electrically coupled to the circuitry 446 through the gates 441-443.

As used herein, the term "layer" is not limited to a single continuous body of material unless otherwise noted. For example, the sensor layer 431 may include multiple sub-layers that are different materials and/or may include coatings, adhesives, and the like. Furthermore, one or more of the layers (or sub-layers) may be modified (e.g., etched, deposited with material, etc.) to provide the features described herein.

In some examples, each light sensor 440 has a detection area that is less than about 50 μm². In particular examples, the detection area is less than about 10 μm². In more particular examples, the detection area is about 2 μm². In such cases, the light sensor 440 may constitute a single pixel. An average read noise of each pixel in a light sensor 440 may be, for example, less than about 150 electrons. In more particular examples, the read noise may be less than about 5 electrons. The resolution of the array of light sensors 440 may be greater than about 0.5 megapixels (Mpixels). In more specific examples, the resolution may be greater than about 5 Mpixels and, more particularly, greater than about 10 Mpixels.

The device layers also include a plurality of metal-dielectric layers 432-437, which are hereinafter referred to as substrate layers. In the illustrated example, each of the substrate layers 432-437 includes metallic elements (e.g., W (tungsten), Cu (copper), or Al (aluminum)) and dielectric material (e.g., $SiO_2$). Various metallic elements and dielectric material may be used, such as those suitable for integrated circuit manufacturing. However, in other examples, one or more of the substrate layers 432-437 may include only dielectric material, such as one or more layers of $SiO_2$.

With respect to the specific example shown in FIG. 8, the first substrate layer 432 may include metallic elements referred to as M1 that are embedded within dielectric material (e.g., $SiO_2$). The metallic elements M1 comprise, for example, W (tungsten). The metallic elements M1 extend entirely through the substrate layer 432 in the illustrated example. The second substrate layer 433 includes metallic elements M2 and dielectric material as well as a metallic interconnects (M2/M3). The third substrate layer 434 includes metallic elements M3 and metal interconnects (M3/M4). The fourth substrate layer 435 also includes metallic elements M4. The device base 425 also includes fifth and sixth substrate layers 436, 437, which are described in greater detail below.

As shown, the metallic elements and interconnects are connected to each other to form at least a portion of the circuitry 446. In the illustrated example, the metallic elements M1, M2, M3, M4 include W (tungsten), Cu (copper), and/or aluminum (Al) and the metal interconnects M2/M3 and M3/M4 include W (tungsten), but it is understood that other materials and configurations may be used. It is also noted that the device base 425 and the detection device 404 shown in FIGS. 7 and 8 are for illustrative purposes only. For example, other examples may include fewer or additional layers than those shown in FIGS. 7 and 8 and/or different configurations of metallic elements.

In some examples, the detection device 404 includes a shield layer 450 that extends along an outer surface 464 of the device base 425. In the illustrated example, the shield layer 450 is deposited directly along the outer surface 464 of the substrate layer 437. However, an intervening layer may be disposed between the substrate layer 437 and the shield layer 450 in other examples. The shield layer 450 may include a material that is to block, reflect, and/or significantly attenuate the light signals that are propagating from the flow channel 418. By way of example only, the shield layer 450 may comprise tungsten (W).

As shown in FIG. 8, the shield layer 450 includes an aperture or opening 452 therethrough. The shield layer 450 may include an array of such apertures 452. In some examples, the shield layer 450 may extend continuously between adjacent apertures 452. As such, the light signals from the flow channel 418 may be blocked, reflected, and/or significantly attenuated to prevent detection of such light signals by the light sensors 440. However, in other examples, the shield layer 450 does not extend continuously between the adjacent apertures 452 such then one or more openings other than the apertures 452 exits in the shield layer 450.

The detection device 404 may also include a passivation layer 454 that extends along the shield layer 450 and across the apertures 452. The shield layer 450 may extend over the apertures 452 thereby directly or indirectly covering the apertures 452. The shield layer 450 may be located between the passivation layer 454 and the device base 425. An adhesive or promoter layer 458 may be located therebetween to facilitate coupling the passivation and shield layers 454, 450. The passivation layer 454 may be to protect the device base 425 and the shield layer 450 from the fluidic environment of the flow channel 418.

In some cases, the passivation layer 454 may also provide a solid surface (i.e., the detector surface 412) that permits biomolecules or other analytes-of-interest to be immobilized thereon. For example, each of the reaction sites 414 may include a cluster of biomolecules that are immobilized to the detector surface 412 of the passivation layer 454. Thus, the passivation layer 454 may be formed from a material that permits the reaction sites 414 to be immobilized thereto. The passivation layer 454 may also comprise a material that is at least transparent to a desired fluorescent light. By way of example, the passivation layer 454 may include silicon nitride ($Si_3N_4$) and/or silica ($SiO_2$). However, other suitable material(s) may be used. In addition, the passivation layer 454 may be physically or chemically modified to facilitate immobilizing the biomolecules and/or to facilitate detection of the light emissions.

In the illustrated example, a portion of the passivation layer 454 extends along the shield layer 450 and a portion of the passivation layer 454 extends directly along filter material 460 of a light guide 462. The reaction recess 408 may be formed directly over the light guide 462. In some cases, prior to the passivation layer 454 being deposited along the shield layer 450 or adhesion layer 458, a base hole or cavity 456 may be formed within the device base 425. For example, the device base 425 may be etched to form an array of the base holes 456. In particular examples, the base hole 456 is an elongated space that extends from proximate the aperture 452 toward the light sensor 440. The base hole may extend lengthwise along a central longitudinal axis 468. A three-dimensional shape of the base hole 456 may be substantially cylindrical or frustro-conical in some examples such that a cross-section taken along a plane that extends into the page of FIG. 8 is substantially circular. The longitudinal axis 468 may extend through a geometric center of the cross-section. However, other geometries may be used in alternative examples. For example, the cross-section may be substantially square-shaped or octagonal.

The filter material 460 may be deposited within the base hole 456 after the base hole 456 is formed. The filter material 460 may form (e.g., after curing) a light guide 462. The light guide 462 is to filter the excitation light 401 and permit the light emissions 466 to propagate therethrough toward the corresponding light sensor 440. The light guide 462 may be, for example, an organic absorption filter. By way of specific example only, the excitation light may be about 532 nm and the light emissions may be about 570 nm or more.

In some cases, the organic filter material may be incompatible with other materials of the biosensor. For example, organic filter material may have a coefficient of thermal expansion that causes the filter material to significantly expand. Alternatively or in addition to, the filter material may be unable to sufficiently adhere to certain layers, such as the shield layer (or other metal layers). Expansion of the filter material may cause mechanical stress on the layers that are adjacent to the filter material or structurally connected to the filter material. In some cases, the expansion may cause cracks or other unwanted features in the structure of the biosensor. As such, examples set forth herein may limit the degree to which the filter material expands and/or the degree to which the filter material is in contact with other layers. For example, the filter material of different light guides may be isolated from each other by the passivation layer. In such examples, the filter material may not contact the metal layer(s). Moreover, the passivation layer may resist expansion and/or permit some expansion while reducing generation of unwanted structural features (e.g., cracks).

The light guide 462 may be provided within surrounding material of the device base 425 (e.g., the dielectric material) to form a light-guiding structure, thereby reducing crosstalk. For example, the light guide 462 may have a refractive index of about 2.0 so that the light emissions are substantially reflected at an interface between the light guide 462 and the material of the device base 425. In certain examples, the light guide 462 is configured such that the optical density (OD) or absorbance of the excitation light is at least about 4 OD. More specifically, the filter material may be selected and the light guide 462 may be dimensioned to achieve at least 4 OD. In more particular examples, the light guide 462 may achieve at least about 5 OD or at least about 6 OD.

Other approaches to reducing crosstalk may, either additionally or alternatively to the light guide 462 or other features of a biosensor 400, be used in some examples. For instance, in some versions, crosstalk between reaction sites may be measured and modeled as an array of values (a "point spread function" or "PSF"). Such a PSF, once determined, may then be used for correcting crosstalk between reaction sites, such as using techniques described in U.S. Pat. App. No. 63/216,125, entitled "Methods and Systems to Correct Crosstalk in Illumination Emitted from Reaction Sites", filed on Jun. 29, 2021, the disclosure of which is incorporated by reference in its entirety. To illustrate how this may take place, consider FIG. 9, which depicts a method in which a PSF may be determined based on images capturing during sequencing of a biological sample and then used to create an optimized sharpening kernel for removing crosstalk from the images.

Figure 9:
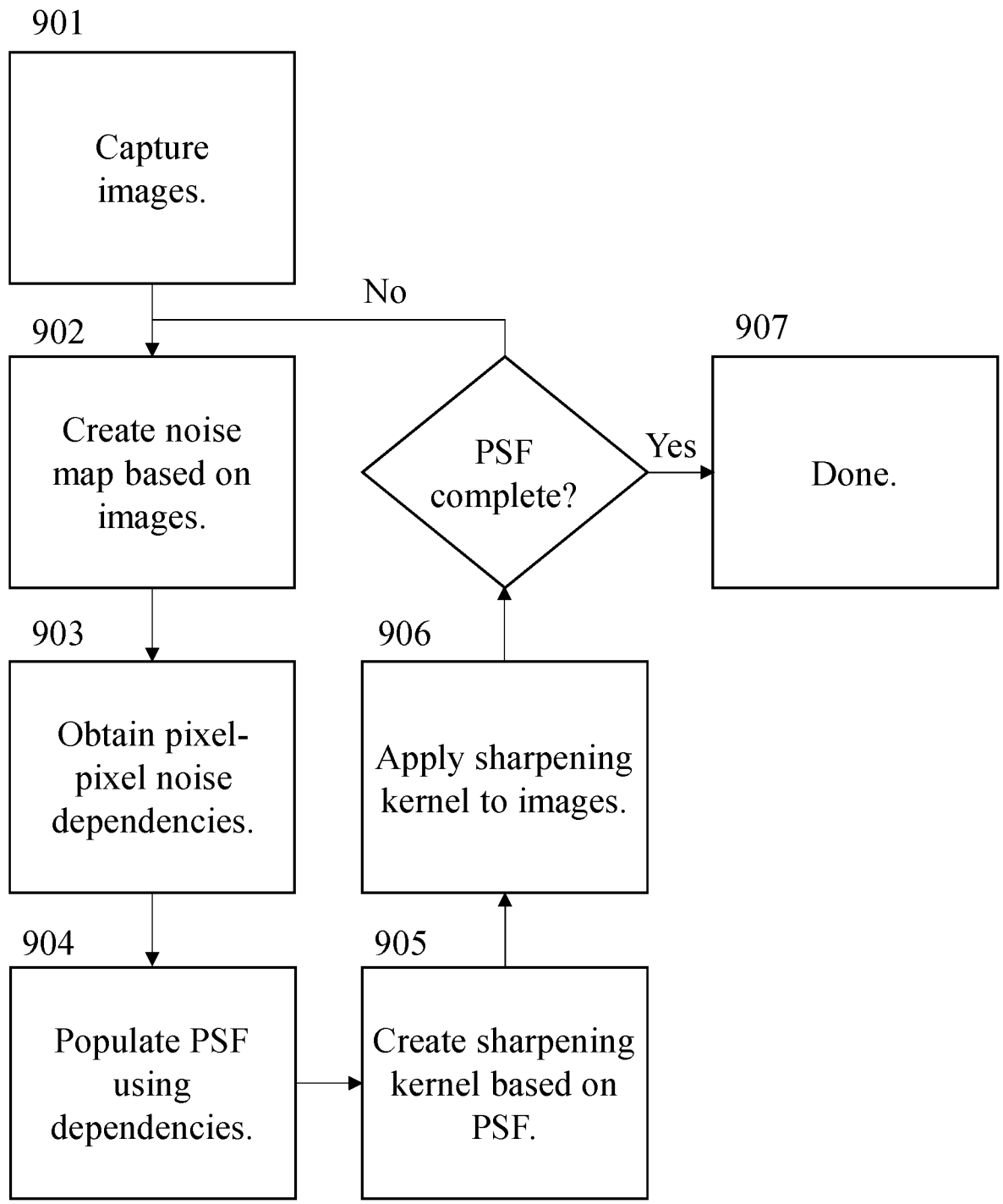
FIG. 9 illustrates a method in which a point spread function may be determined.

In the method of FIG. 9, initially images are captured in block 901, such as during sequencing of a biological sample by a bioassay system 100 as depicted in FIG. 1. These images may be used in block 902 to create a noise map which, as described, may be used in identifying noise in the form of signals which have leaked into surrounding pixels. This may be done, for example by capturing two images, and subtracting one image from the other as shown in FIG. 10 which illustrates how a first image 1001 made up of a first M×N array of intensity values may be subtracted from a second image 1002 made up of a second M×N array of intensity values, to provide a noise map 1003 in the form of a M×N array of differences. Next, in block 903, this noise map may be used to obtain noise dependences between pixels from the original images. A process which may be used for performing this step is provided in FIG. 11, discussed below.

Figure 11:
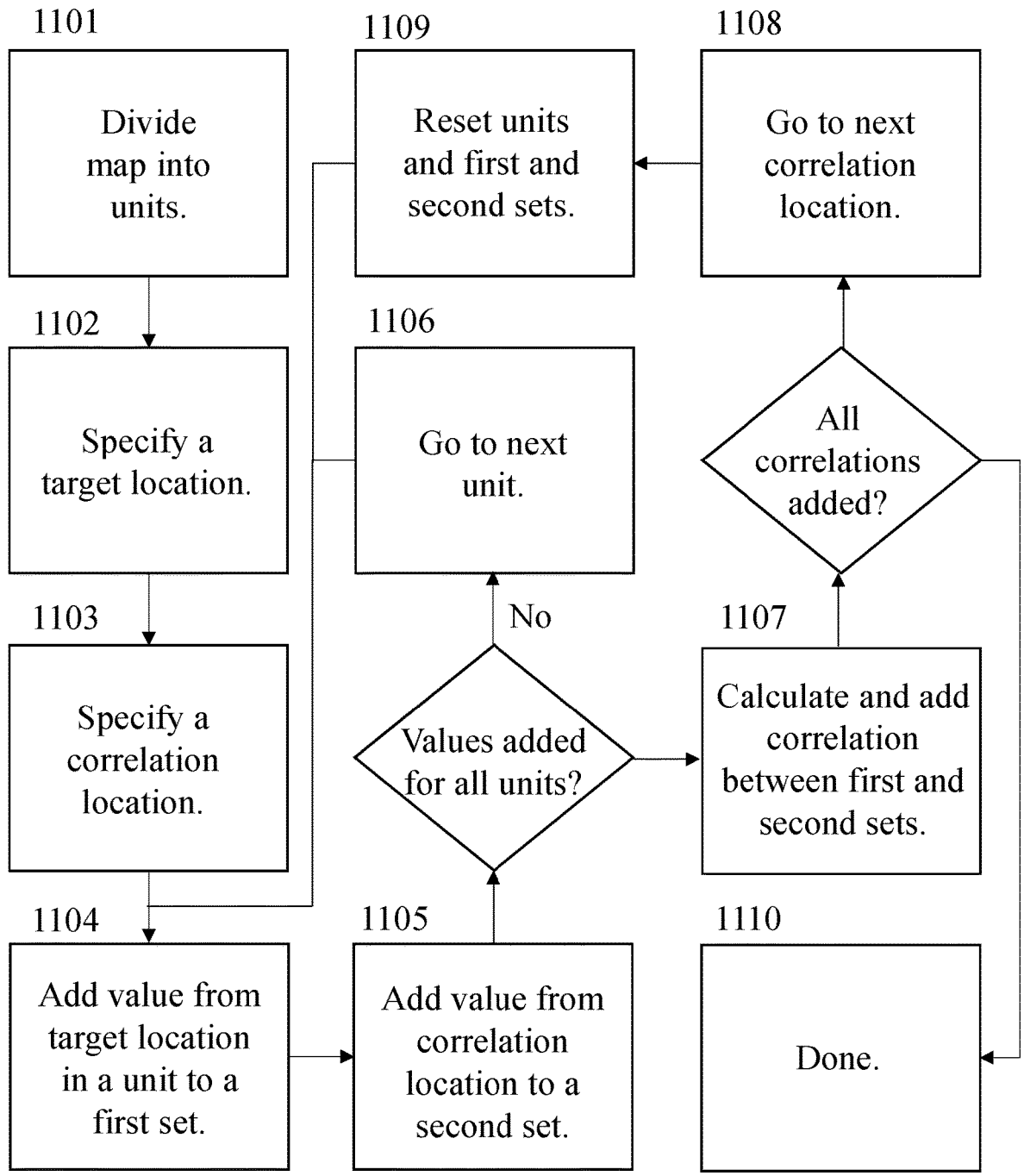
FIG. 11 illustrates a process which may be used to calculate noise dependencies between pixels.

A process such as shown in FIG. 11 may start in block 1101 with dividing the noise map created in block 902 from FIG. 9 into a set of units. For example, if the noise map is a 700×700 array, then the division of the noise map into units may be performed by separating the noise map into 10,000 7×7 units. Preferably, these units would have dimensions at least as great as those of the PSF to be created. For example, if the PSF is to be created in the form of a 5×5 matrix, then the noise map may be split into 5×5, 6×6, 7×7 or 8×8 units. Units having different shapes than the ultimate PSF may also be possible, such as 5×6, 6×5, 5×7, etc. units. Next, in block 1102, a target location is specified. This may be done, for example, by specifying that a location corresponding to the center of a unit would be the target location. For instance, in a case where units are 7×7 or 8×8 squares, the target location may be (4,4). In general, this target location may be specified such that the distance between the target location and the closest edge of a unit would be no less than the distance from the center to the edge of a PSF to be determined by the process of FIG. 9. After the target location is specified, in block 1103 a correlation location would be specified. This may be done, for example, by specifying a location corresponding to a top-leftmost corner of a unit (e.g., (1,1)), though other approaches (e.g., specifying another corner as the correlation location, or specifying the correlation location at random) may also be implemented.

Figure 12:
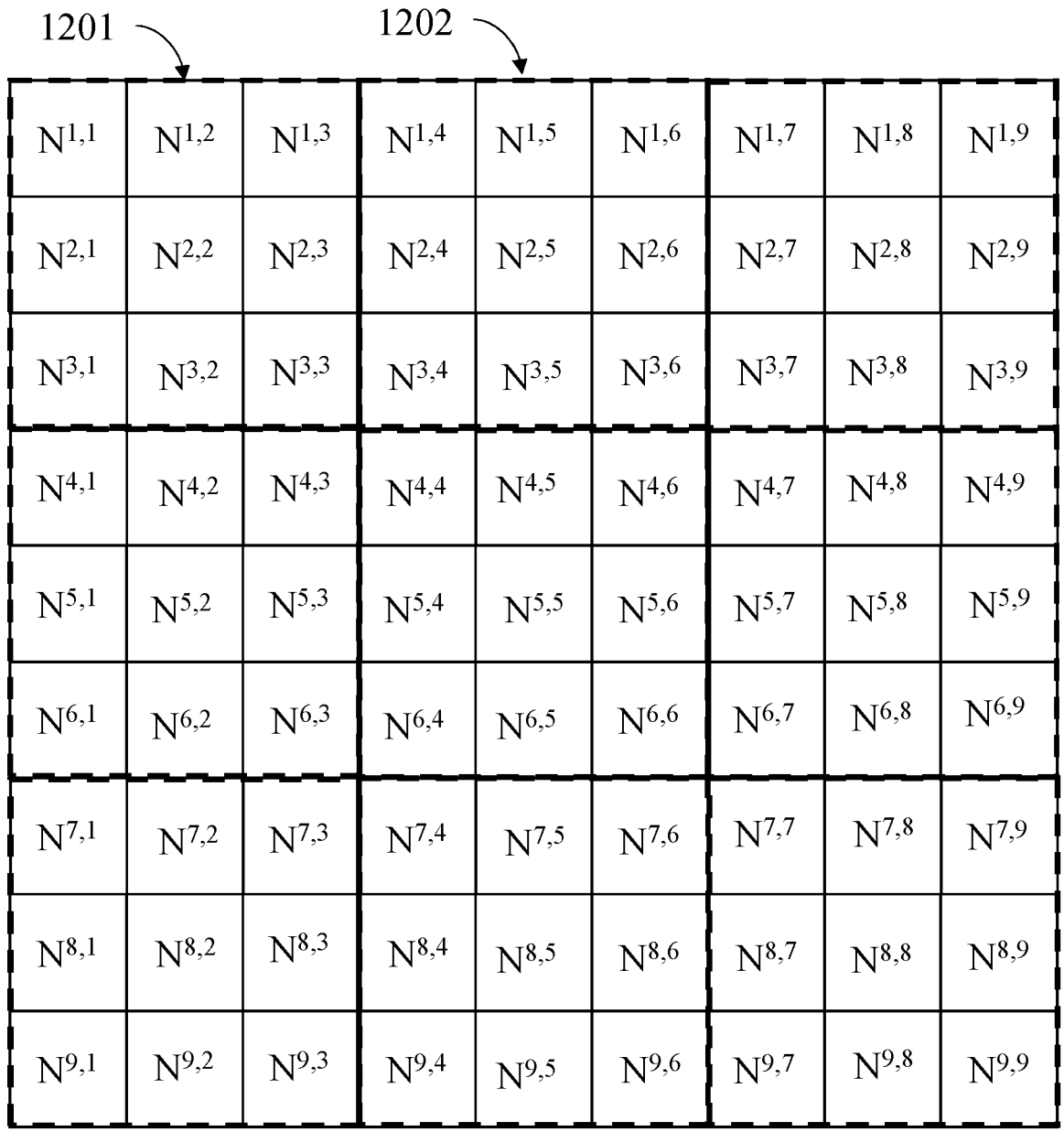
FIG. 12 illustrates an example 9×9 noise map split into 9 3×3 units.

After target and correlation locations had been specified in block 1102 and block 1103, a value from the target location in a unit is added to a first set in block 1104. For instance, in the example 9×9 noise map split into 9 3×3 units shown in FIG. 12, adding a value from the target location in a unit to a first set may be performed by taking the value $N^{2,2}$ from the center of the unit 1201 in the upper left corner of the noise map, and adding it to a first set. Then, in block 1105, a value from the correlation location would be added to a second set. To continue with the previous example, if the value $N^{2,2}$ had been added to the first set in block 1104, and (1,1) had been specified as the correlation location in block 1103, then the value $N^{1,1}$ could be added to the second set in block 1105. Then, if a value had not been added for all of the units in the noise map, in block 1106 the process of FIG. 11 could proceed to the next unit. This may be done, for example, by proceeding to the left neighbor of the unit from which values had just been added to the first and second sets (e.g., the upper middle unit 1202 in the noise map of FIG. 12), though other approaches may also be possible (e.g., proceeding to a randomly selected unit from which values had not been added, proceeding to the leftmost unit of the column below the column of the unit from which values had been added, etc.). The process could then iterate, repeating blocks 1104-1106 until values had been added for the target location and the correlation location for all of the units in the noise map.

In the process of FIG. 11, after values had been added to the first and second sets for each of the units in the noise map, a correlation between those sets could be calculated and added to a matrix having the same size as a unit in block 1107. To illustrate, consider the example of FIG. 12. If iteration through blocks 1104-1106 had resulted in the following first and second sets being created for target location (2,2) and correlation location (1,1):

| First Set | Second Set | |
|---|---|---|
| [$N^{2,2}$] | [$N^{1,1}$] | (center and upper left values from upper left unit) |
| [$N^{2,5}$] | [$N^{1,4}$] | (center and upper left values from upper middle unit) |
| [$N^{2,8}$] | [$N^{1,7}$] | (center and upper left values from upper right unit) |
| [$N^{5,2}$] | [$N^{4,1}$] | (center and upper left values from middle left unit) |
| [$N^{5,5}$] | [$N^{4,4}$] | (center and upper left values from center unit) |
| [$N^{5,8}$] | [$N^{4,7}$] | (center and upper left values from middle right unit) |
| [$N^{8,2}$] | [$N^{7,1}$] | (center and upper left values from lower left unit) |
| [$N^{8,5}$] | [$N^{7,4}$] | (center and upper left values from lower middle unit) |
| [$N^{8,8}$] | [$N^{7,7}$] | (center and upper left values from lower right unit) | and if the correlation between those sets was equal to $C_{1,1}$, then that value could be added to a 3×3 matrix as shown below (with \0 being used to denote undefined elements):

[$C_{1,1}$ \0 \0]
[\0 0 \0]
[\0 \0 \0]

After the correlation for the current correlation location had been calculated and added in block 1107, if there were still correlations to add (e.g., if there was at least one location in a unit, other than the target location, for which a correlation had not been calculated and added), then, in block 1108, the process of FIG. 11 could proceed to the next correlation location. This may be done in a manner similar to that described in the context of block 1106 for proceeding to the next unit, except instead of proceeding to a new unit for which values hadn't been added to the first and second sets, in block 1108 the process may proceed to a correlation location (e.g., any location other than the target location) for which a correlation hadn't been calculated. The first and second sets, and units could then be reset in block 1109—e.g., all values added to the first and second sets during the previous iterations of steps 1104-1106 could be removed, and whatever data was used to track what units had had values added to the first and second sets could be set to indicate that the first and second sets were empty. The process may then iterate through blocks 1104-1106 with the new correlation location, and this may continue until values had been calculated and added for all locations, at which point the process could terminate in block 1110 and the matrix of correlation values could be treated as pixel-pixel noise dependencies for each location in a unit relative to the target location.

Figure 13A:
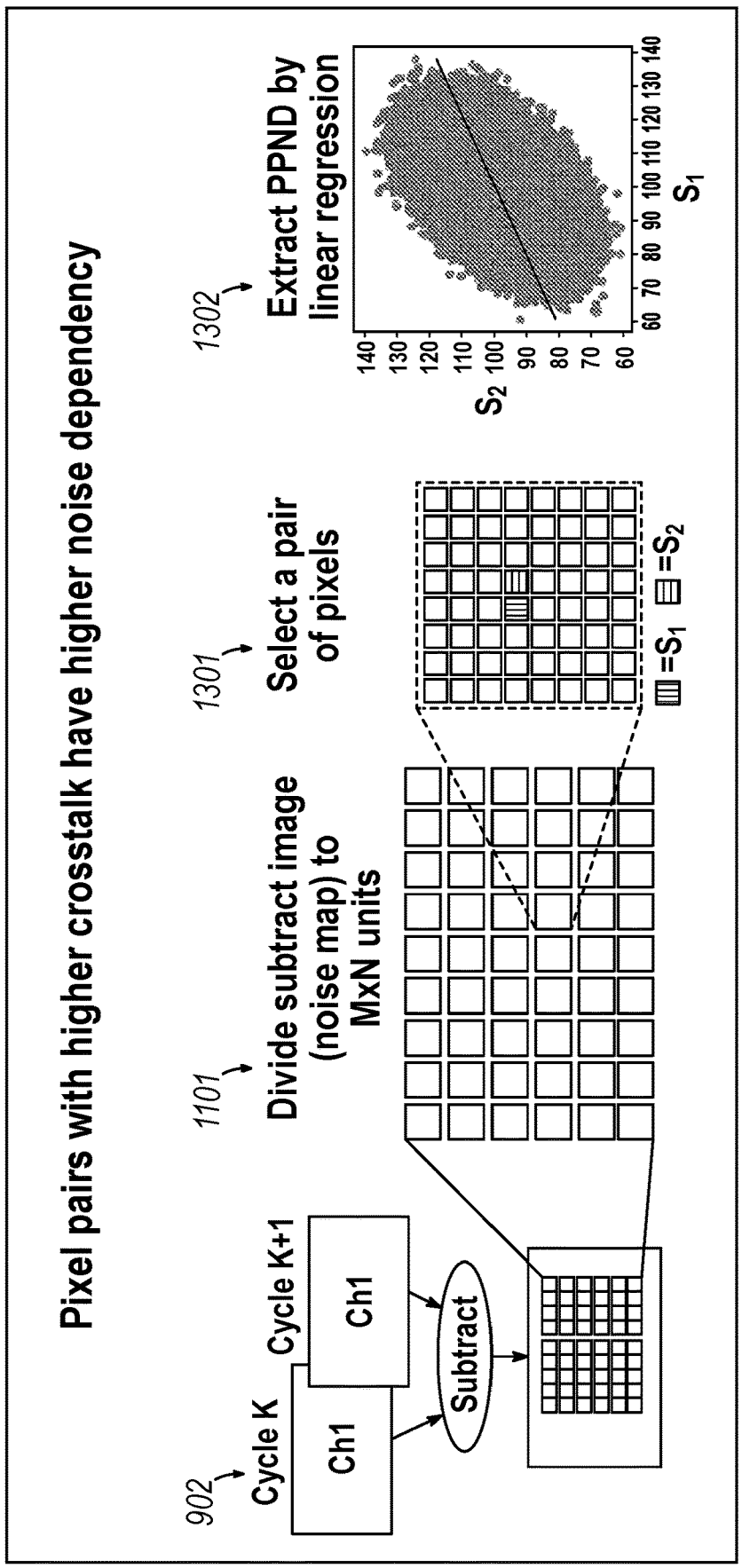
FIGS. 13A-13C provide illustrations of how pixel to pixel noise dependencies may be captured.
Figure 13B:
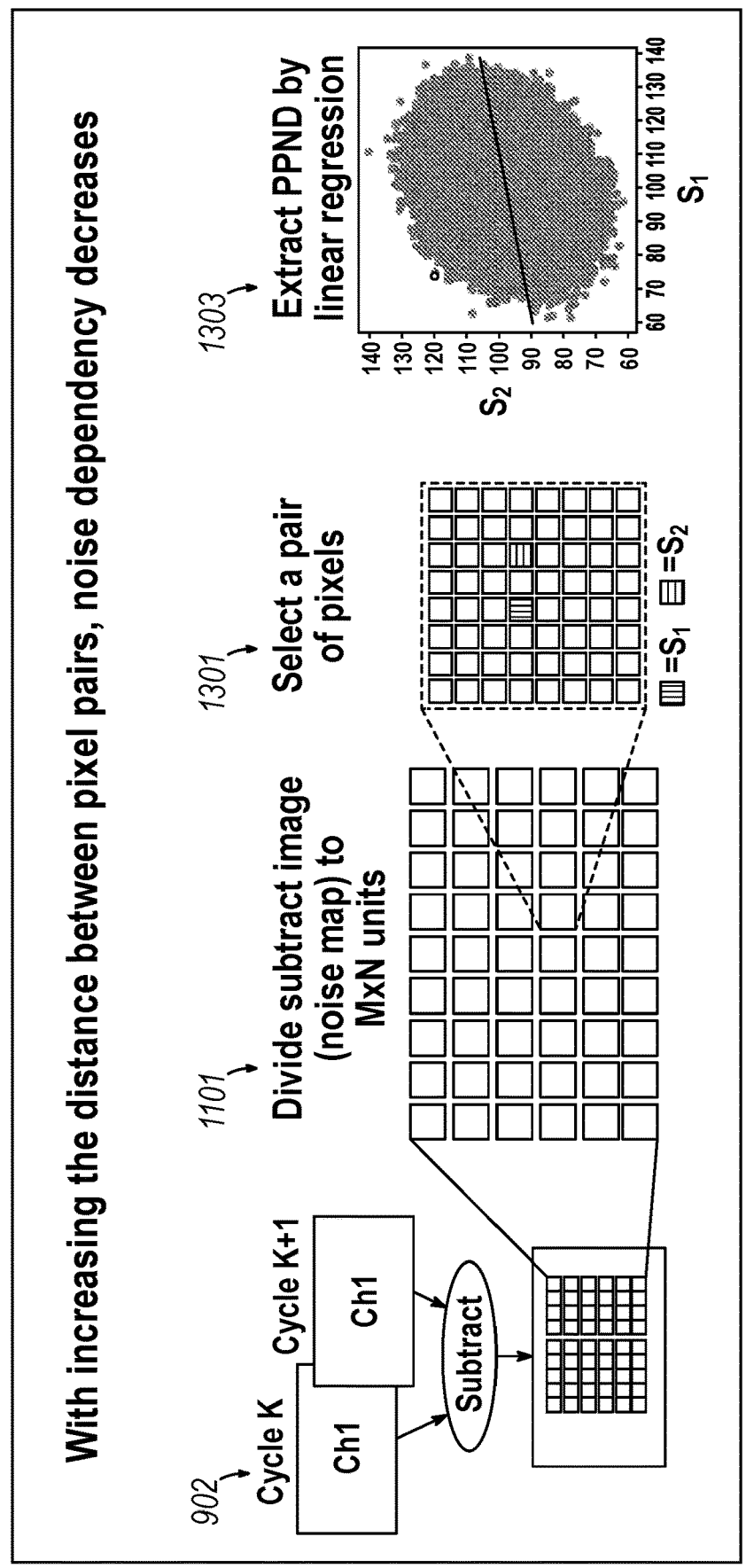
Figure 13C:
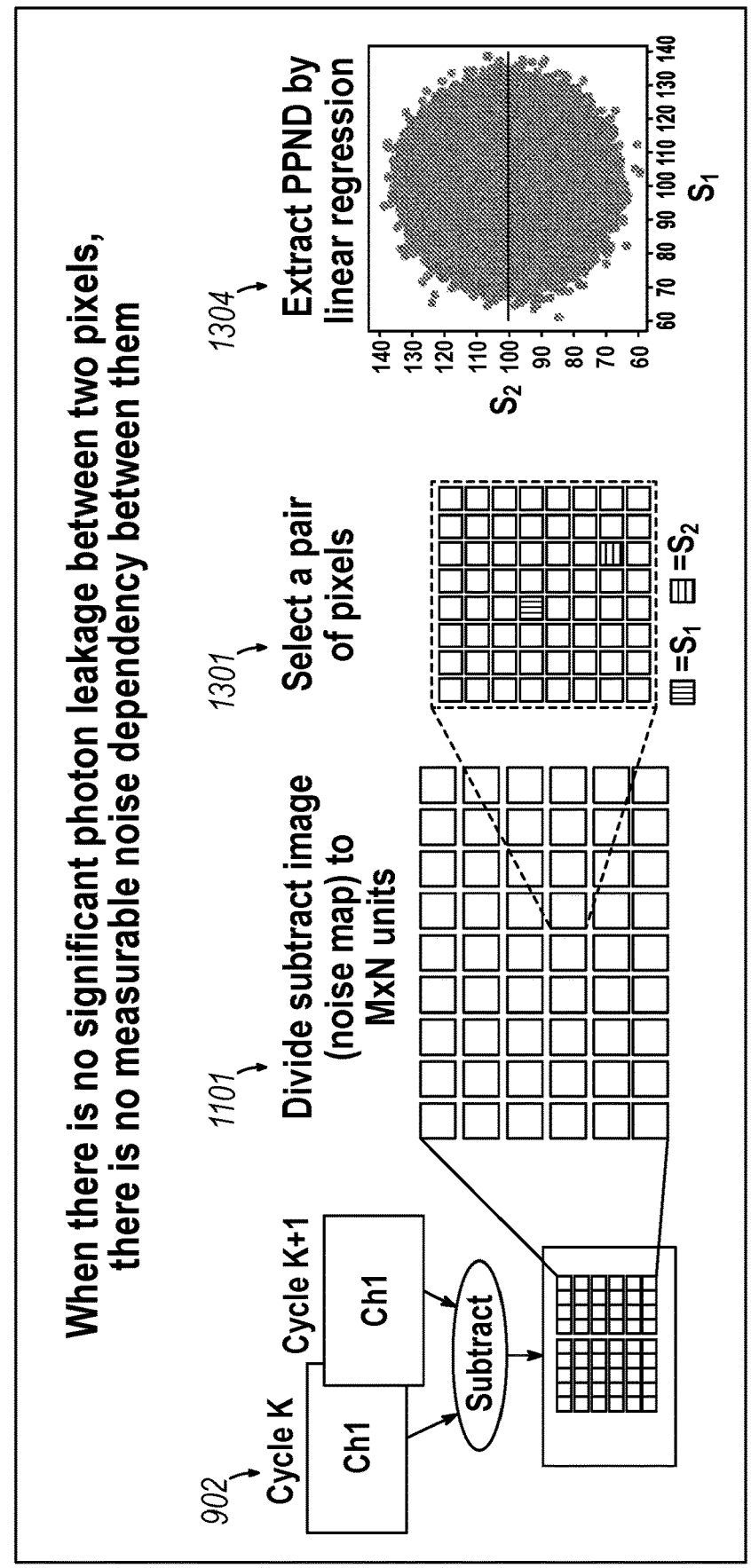

A further illustration of how pixel to pixel noise dependencies may be derived from captured images is provided in FIGS. 13A-13C. Those figures illustrate how a noise map may be created as described previously in the context of block 902 based on images captured on different cycles, how it may be divided into units as described previously in the context of block 1101, and how the specification of target and correlation locations as described previously in the context of blocks 1102 and 1103 can be conceived as selection of a pair of pixels 1301. FIGS. 13A-13C also illustrate that the calculation of a correlation between pixel values can be performed using linear regression, and that the greater the distance between the target and correlation locations, the lower the dependency between their values (as shown in the correlation graphs 1302 1303 1304 of FIGS. 13A-13C). It should be noted that, while FIGS. 13A-13C illustrate the calculation of a correlation between pixel values as being performed using linear regression, other types of calculation may also be used when obtaining 903 pixel to pixel noise dependencies. For example, nonlinear regressions may alternatively be used in some cases. Accordingly, the examples provided in FIGS. 13A-13C should be understood as being illustrative only, and should not be treated as limiting.

Figure 14:
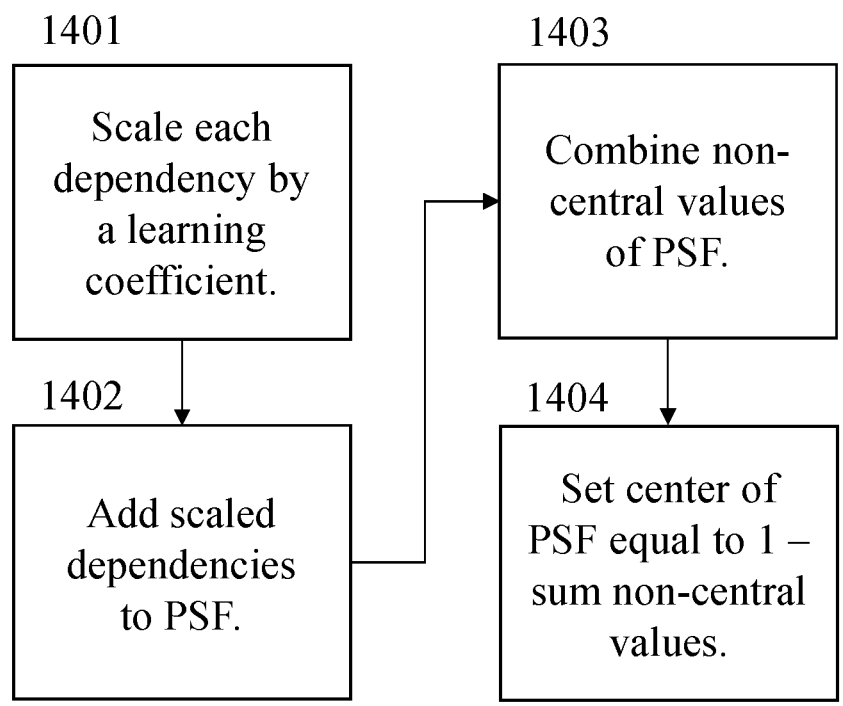
FIG. 14 illustrates a process in which pixel-pixel noise dependencies may be used to populate a point spread function.

Returning now to the process of FIG. 9, after pixel-pixel to pixel noise dependencies had been obtained in block 903, those dependencies may be used to populate a PSF in block 904. This may be done, for example, using a process such as shown in FIG. 14. In that process, in block 1401, each of the pixel-pixel noise dependencies may be scaled by a learning coefficient. This may be done, for example, by multiplying each value in a matrix such as may be created by a process such as shown in FIG. 11 by a value between 0.01 and 0.25. These values may be, for example, 0.8, 0.12, 0.15, values between 0.15 and 0.25, or other values such as may be used to control how much influence data may have on a learning process, with lower values generally requiring more iterations, but higher values running a greater risk that the learning process will fail to converge.

After the dependencies had been scaled, they may then be added to the PSF in block 1402. This may be done, for example, on a first iteration, by mapping the target location in a matrix as may be created by a process such as shown in FIG. 11 to the center of the PSF, and then overlaying the scaled dependency values from the matrix onto the PSF. Subsequently, this may be done by performing a similar type of mapping, except instead of simply overlaying the scaled dependency values onto the corresponding locations in the PSF, adding those scaled dependency values to the values in the corresponding locations of the PSF as determined on the preceding iteration. Essentially, this may be represented by the equation $PSF^{N+1}=PSF^N+r*PPND$, in which PPND is the pixel-to-pixel noise dependencies obtained in block 903, r is the learning coefficient, $PSF^N$ is a zero matrix on the first iteration and is the PSF from the preceding iteration on every iteration thereafter, and $PSF^{N+1}$ is the PSF that would be created as a result of adding the scaled dependencies in block 1402. Then, once the scaled dependency values had been added to the PSF, the values of the PSF other than the value at the PSF's center may then be combined in block 1403, and a value equal to 1 minus that sum may be inserted at the PSF's center in block 1404.

Other approaches to populating a PSF using pixel to pixel noise dependencies may also be used. For example, just as FIG. 14 illustrated the application of a learning constant to each dependency in block 1401, in some implementations other types of transformations may also be applied. For example, each dependency may be transformed by a non-linear function (e.g., each dependency may be cubed, each dependency may be replaced by its log, etc.), which may have the effect of making a PSF derived from the dependency matrix more sensitive to asymmetry, such as where the dependencies are calculated using linear regressions. Similarly, while the above description explained that $PSF^N$ may be a zero matrix on the first iteration, it is also possible that on the first iteration $PSF^N$ may be a matrix having a one at its center and all other elements set as zero, or that it may be an estimate of the likely PSF (e.g., based on the PSF derived for other similar systems) that would then be refined using the PPND as described. Accordingly, FIG. 14 and the associated discussion should be understood as being illustrative only, and should not be treated as implying limits on the protection provided by this document or any related document.

After the PSF had been populated in block 904, a sharpening kernel may be created based on that PSF in block 905. This may be done, for example, by inverting the PSF, by using sharpening kernel creation techniques such as described in U.S. Pat. App. No. 63/216,125, entitled "Methods and Systems to Correct Crosstalk in Illumination Emitted from Reaction Sites", filed on Jun. 29, 2021, or in other manners as may be appropriate in a particular case. In block 906, this sharpening kernel may then be applied to the images captured previously in block 901 to obtain one or more sharpened images. Those sharpened images may then be used to determine whether the process of determining the PSF should be treated as complete. This may be done, for example, by measuring the signal to noise ratio (SNR) in the sharpened image(s) (e.g., by testing the sharpness of those images), and comparing it with the SNRs in sharpened images created on previous iterations of the process (if any). In this type of comparison approach, if the SNR of the sharpened image(s) is less than or equal to the SNR of sharpened image(s) created in a preceding iteration, then the PSF determination may be treated as complete, with the PSF created on the iteration whose sharpened image(s) had the highest SNR being treated as the correct PSF. As another example, in some cases, the PSF determination may be treated as complete when a set number of iterations had been finished (e.g., iteration 4 for a learning coefficient of 0.12, iteration 5 for a learning coefficient of 0.08), or may be treated as complete when the SNR of the sharpened images reached or exceeded a particular threshold (e.g., SNR meeting or exceeding 0.9). As another example, in some cases, the PSF determination may be treated as complete by comparing PSFs and stopping when the PSFs no longer change, or when their values when summed across the PSF change by less than some threshold (e.g., 1%) across iterations. Other approaches to determining when to treat the process as complete (e.g., a hybrid, where reaching a set number of iterations, or satisfying a PSF comparison condition, or satisfying a SNR comparison condition) may also be used, will be immediately apparent to, and could be implemented without undue experimentation by those of ordinary skill in the art based on this disclosure. Accordingly, the discussion above should be understood as being illustrative only, and should not be treated as limiting.

In a process such as shown in FIG. 9, if it is determined that the PSF creation is complete, then the process may terminate in block 907, such as by treating the PSF associated with the sharpening kernel that created the sharpened image(s) with the highest SNR as the correct PSF, and treating the sharpening kernel created based on that PSF as the correct sharpening kernel to use in removing crosstalk from images during a sequencing cycle. Alternatively, if it is determined that the PSF creation is not complete, then the process may iterate, returning to block 902 and using the sharpened images created during the most recent performance of block 906 to create a noise map, obtaining new pixel to pixel noise dependencies in block 903 using this new noise map, populating a new PSF in block 904 by adding those dependencies to the PSF from the previous iteration, creating a new sharpening kernel with that new PSF in block 905, and then, in block 906, applying that sharpening kernel to the images originally captured in block 901. This may then be repeated one or more times until it was determined that PSF creation was complete, at which point the process may complete in as described above in block 907.

Figure 15:
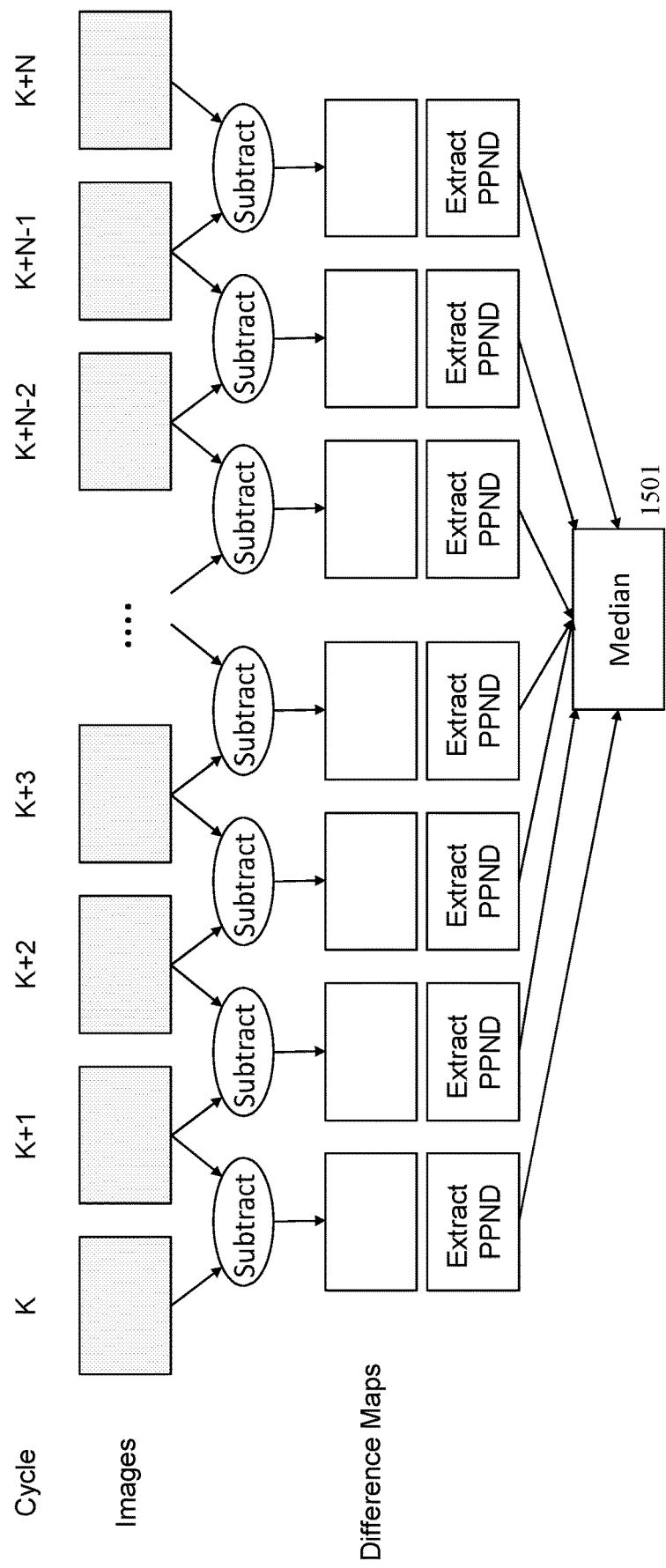
FIG. 15 illustrates a process in which more than two images are used to create a collective set of pixel to pixel noise dependencies.

It should be understood that, while the above examples have illustrated how point spread functions may be determined in real time during an imaging run, the above examples are not intended to be exclusive, and other approaches may also be possible. For example, while the process of FIG. 9 may be implemented in a manner which populates a PSF in block 904 using pixel to pixel noise dependencies calculated using a noise map created in block 902 based on subtracting one image from another, it is possible that additional images may be incorporated into this process as well. To illustrate, consider FIG. 15, which illustrates an approach in which more than two images are used to create difference maps, which are then used to calculate multiple sets of noise dependencies, which are then combined (shown in FIG. 15 as calculating the median, though other approaches, such as averaging, may also be utilized) to provide a collective PPND 1501. This collective PPND 1501 may be used in block 904 for populating a PSF, potentially providing for a more accurate determination based on the use of more information from the multiple images in creating the collective PPND 1501.

Other variations may also be possible. For instance, consider a case where a biosensor used to capture images is manufactured in such a way that its light sensors could be expected to exhibit periodic variation in their PSFs. To illustrate, consider FIG. 16, which illustrates four PSFs, labeled odd_odd, odd_even, even-odd, and even-even. It may be the case that, in a biosensor having a rectangular array of light sensors, the PSF for all light sensors in odd rows and columns (e.g., the sensor at positions (1,1), (1,3), (1,5), (3,1), (3,3), etc.) may be odd_odd, the PSF for all light sensors in odd rows and even columns may be odd_even, the PSF for all light sensors in even rows and odd columns may be even-odd, and the PSF for all light sensors in even rows and columns may be even-even. In this type of scenario, all sensors may be treated as having a single PSF, such as by averaging the actual PSFs and applying the averaged PSF to all sensors. However, it may also be possible to account for the variation in PSFs to improve the accuracy of the PDF calculation. An example of how this may be done is discussed below.

In some cases, a system implemented based on this disclosure may account for even-odd periodicity in a sensor array by modifying the PSF determination process such as shown in FIG. 9. In making this type of modification, portions of the process of FIG. 9 which would be impacted by the periodicity—e.g., the obtaining of pixel-pixel noise dependencies in block 903, the PSF population on block 904, the creation of a sharpening kernel in block 905, and the application of the sharpening kernel in block 906—may be modified to reflect the periodicity. For example, the obtaining of pixel-pixel noise dependencies in block 903 may be modified from calculating a single matrix of noise dependencies as described previously, to calculating multiple matrices, one for each class of sensor. In the case of even-odd periodicity, this may include calculating a first matrix where the target location is an odd-odd location, a second matrix where the target location is an odd-even location, a third matrix where the target location is an even-odd location, and a fourth matrix where the target location is an even-even location. These matrices may then be used in a modified version of block 904 to populate multiple PSFs—e.g., one for each class of sensor. These multiple PSFs may be used to create multiple sharpening kernels in a modified version of block 905, and those multiple sharpening kernels may be applied to the images in a modified version of block 906. In this way, performance of a process such as shown in FIG. 9 could result in multiple PSFs and sharpening kernels, as opposed to only a single PSF and sharpening kernel as described previously.

Figure 17:
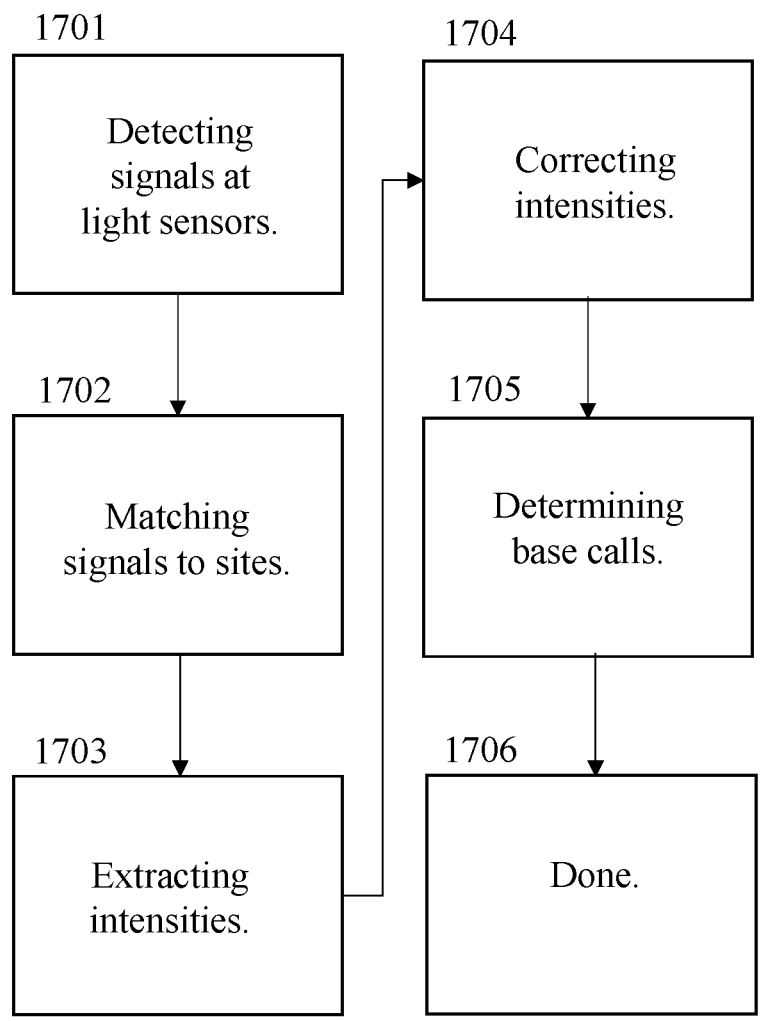
FIG. 17 illustrates a primary analysis process in which sharpening kernels may be applied to address crosstalk.

Another example of a type of variation which may exist between applications of aspects of the disclosed technology is variation in structure of implementation. For example, in some cases, the generation of PSFs such as described above may be performed in the context of a process illustrated in FIG. 17 and referred to as primary analysis or real time analysis on a bioassay system 100 itself. In this type of process, in block 1701, signals are detected at light sensors, e.g., light sensors 440 of a biosensor 400. In block 1702, those signals are matched to sites. This may be performed in a variety of manners. For example, as noted in U.S. Patent Publ. No. 2020/0080142, the disclosure of which is hereby incorporated by reference in its entirety, a location template may be generated and used to register reaction sites with captured signals. Similarly, either in addition to, or as an alternative to, this type of registration, block 1702 may also include computationally correcting inter-site crosstalk such as by extracting PSFs and using them to generate sharpening kernels using processes such as described above in the context of FIG. 9, so as to reduce the impact of light emitted from one reaction site on the signal associated with other reaction sites in its immediate vicinity. The intensities of the various signals may then be extracted in block 1703, for example, by detecting regions in an inter-site crosstalk corrected image where signals exceeding a specified background intensity are detected. These extracted intensities may then be subjected to further correction in block 1704, such as through correction of inter-channel crosstalk as described in U.S. Pat. No. 10,304,189 and U.S. Patent Publ. No. 2020/0080142, each of which is incorporated by reference in its entirety. Once all necessary corrections had been applied, they may be used in block 1705 for determining base calls. This base call information may then be outputted in the form of base call files storing nucleic acid (DNA, RNA) sequencing information, and, at block 1706, the process of FIG. 17 may terminate.

However, the extraction of PSFs as part of real time analysis on a bioassay system may not be included in all implementations. For example, in some cases, a manufacturer of a biosensor may obtain PSFs using techniques described herein, use them to create sharpening kernels, and store the sharpening kernels in memory on a biosensor. Later, when the biosensor was used for analyzing a substance, those sharpening kernels may be applied using the biosensor's circuitry to obtain crosstalk corrected values which may then be provided to (and applied by) the controller of a bioassay system.

Other types of variations may also be possible. For example, in some implementations, a biosensor may be manufactured which omits one or more features designed to minimize crosstalk, such as omitting light guides 462 of the detection device 404, relying on computational methods such as described herein instead of physical structures to address crosstalk. Similarly, aspects of the disclosed technology may also be applied in contexts other than bioassay systems. For example, other types of imaging systems, such as digital cameras may also experience crosstalk in which photons for one imaging element will be detected by another imaging element, and the disclosed technology may be applied to compensate for crosstalk in such signals in a manner similar to how it may be applied in bioassay systems. Accordingly, the examples provided herein should be understood as being illustrative only, and should not be treated as limiting on the protection provided by this document or any related document.

It is to be understood that the subject matter described herein is not limited in its application to the details of construction and the arrangement of components set forth in the description herein or illustrated in the drawings hereof. The subject matter described herein is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

When used in the claims, the term "set" should be understood as one or more things which are grouped together. Similarly, when used in the claims "based on" should be understood as indicating that one thing is determined at least in part by what is specified as being "based on". Where one thing is required to be exclusively determined by another thing, then that thing will be referred to as being "EXCLUSIVELY based on" that which it is determined by.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "above," "below," "front," "rear," "distal," "proximal," and the like) are only used to simplify description of one or more examples described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described examples (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and instead illustrations. Many further examples will be apparent to those of skill in the art upon reviewing the above description. The scope of the disclosed subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. In that vein, "means for generating a point spread function based on images captured using the sensor array during real time analysis of a biological sample" should be understood as a means plus function limitation as set forth in 35 U.S.C. § 112(f), in which the function is generating a point spread function based on images captured using the sensor array during real time analysis of a biological sample" and the corresponding structure is a computer to perform processes as shown and discussed in the context of FIG. 9.

The following claims recite aspects of certain examples of the disclosed subject matter and are considered to be part of the above disclosure. These aspects may be combined with one another.

What is claimed is:

1. A method comprising:
obtaining a plurality of analysis images of light emitted during sequencing of a biological sample;
obtaining noise dependencies by performing acts comprising, for each location in a point spread function which comprises a plurality of locations, calculating a noise correlation for that location, wherein the noise correlation is a correlation between noise in a first plurality of measurements and noise in a second plurality of measurements, wherein:
each measurement from the first plurality of measurements is captured by a sensor whose position relative to a corresponding sensor which captured a measurement from the second plurality of measurements is the same as that location's position in the point spread function relative to a center of the point spread function; and
each measurement from the first plurality of measurements and the second plurality of measurements measures light emitted during sequencing of the biological sample from the plurality of analysis images;
populating the point spread function based on the noise dependencies;
generating a sharpening kernel based on the point spread function;
obtaining a plurality of sharpened images by applying the sharpening kernel to the plurality of analysis images;
one or more times, repeating:
obtaining noise dependencies;
populating the point spread function;
generating the sharpening kernel; and
obtaining the plurality of sharpened images;
wherein, on each repetition, the plurality of analysis images for that repetition of obtaining noise dependencies is the plurality of sharpened images from a most recent preceding application of the sharpening kernel;
identifying a sharpening kernel generated on a repetition as an optimal sharpening kernel; and
applying the optimal sharpening kernel to compensate for crosstalk in images subsequently captured while sequencing the biological sample.

2. The method of claim 1, wherein repeating populating the point spread function comprises:
generating a dependency matrix having dimensions equal to those of the point spread function by, for each location in the point spread function, populating a corresponding location in the dependency matrix with a most recently obtained dependency for that location;
multiplying the dependency matrix by a scalar constant; and
adding a result of multiplying the dependency matrix by the scalar constant to a most recently populated preceding point spread function.

3. The method of claim 2, wherein the scalar constant has a value greater than or equal to 0.08, and less than or equal to 0.12.

4. The method of claim 1, wherein identifying the optimal sharpening kernel comprises:
determining, for each repetition, a signal to noise ratio obtained by applying the sharpening kernel generated on that repetition to the plurality of analysis images; and
identifying the sharpening kernel from which a highest signal to noise ratio is obtained as the optimal sharpening kernel.

5. The method of claim 4, wherein determining, for each repetition, the signal to noise ratio comprises calculating a sharpness of the plurality of sharpened images obtained on that repetition.

6. The method of claim 1, wherein obtaining noise dependencies comprises obtaining a noise map based on subtracting a first image from the plurality of analysis images from a second image from the plurality of analysis images.

7. The method of claim 6, wherein:
obtaining noise dependencies comprises dividing the noise map into a plurality of units, wherein each unit is a matrix of values having dimensions at least as great as those of the point spread function;
for each location in the point spread function, obtaining the noise dependency for that location comprises calculating a correlation between a first set of values and a second set of values, wherein:
the first set of values comprises, for each unit from the plurality of units, a value at a first location in that unit; and
the second set of values comprises, for each unit from the plurality of units, a value at a second location in that unit, wherein the first location for the value from that unit in the first set of values has a position relative to the second location that is the same as that location's position in the point spread function relative to the center of the point spread function.

8. The method of claim 6, wherein:
the first image from the plurality of analysis images is an image captured from a first sequencing cycle; and
the second image from the plurality of analysis images is an image from a second sequencing cycle.

9. The method of claim 1, wherein:
each image from the plurality of analysis images comprises an image from a different sequencing cycle;
the plurality of analysis images comprises more than two images;
obtaining noise dependencies comprises:
obtaining a plurality of intermediate correlations, wherein each of the intermediate correlations corresponds to two analysis images from the plurality of analysis images, and wherein each of the plurality of intermediate correlations is obtained based on:
obtaining an intermediate map for that intermediate correlation by subtracting one of the analysis images corresponding to that intermediate correlation from the other analysis image corresponding to that intermediate correlation;
dividing the intermediate map for that intermediate correlation into a plurality of units, wherein each unit is a matrix of values having dimensions at least as great as those of the point spread function;
for each location in the point spread function, calculating a correlation between a first set of values and a second set of values, wherein:
the first set of values comprises, for each unit from the plurality of units, a value at a first location in that unit; and
the second set of values comprises, for each unit from the plurality of units, a value at a second location in that unit, wherein the first location for the value from that unit in the first set of values has a position relative to the second location that is the same as that location's position in the point spread function relative to the center of the point spread function;
determining the set of noise dependencies based on the plurality of intermediate correlations.

10. The method of claim 1, wherein obtaining noise dependencies, populating the point spread function, generating the sharpening kernel, and obtaining the plurality of sharpened images are repeated between two and eight times.

11. A system comprising:
a sensor array;
a processor to:
obtain a plurality of analysis images of light emitted during sequencing of a biological sample;
obtain noise dependencies by performing acts comprising, for each location in a point spread function which comprises a plurality of locations, calculating a noise correlation for that location, wherein the noise correlation is a correlation between noise in a first plurality of measurements and noise in a second plurality of measurements, wherein:
each measurement from the first plurality of measurements is captured by a sensor from the sensor array whose position relative to a corresponding sensor in the sensor array which captured a measurement from the second plurality of measurements is the same as that location's position in the point spread function relative to a center of the point spread function; and
each measurement from the first plurality of measurements and the second plurality of measurements measures light emitted during sequencing of the biological sample from the plurality of analysis images;
populate the point spread function based on the noise dependencies;
generate a sharpening kernel based on the point spread function;
obtain a plurality of sharpened images by applying the sharpening kernel to the plurality of analysis images;
one or more times, repeat:
obtaining noise dependencies;
populating the point spread function;
generating the sharpening kernel; and
obtaining the plurality of sharpened images;
wherein, on each repetition, the plurality of analysis images for that repetition of obtaining noise dependencies is the plurality of sharpened images from a most recent preceding application of the sharpening kernel;
identify a sharpening kernel generated on a repetition as an optimal sharpening kernel; and
apply the optimal sharpening kernel to compensate for crosstalk in images subsequently captured while sequencing the biological sample.

12. The system of claim 11, wherein repeating populating the point spread function comprises:
generating a dependency matrix having dimensions equal to those of the point spread function by, for each location in the point spread function, populating a corresponding location in the dependency matrix with a most recently obtained dependency for that location;
multiplying the dependency matrix by a scalar constant; and
adding a result of multiplying the dependency matrix by the scalar constant to a most recently populated preceding point spread function.

13. The system of claim 12, wherein the scalar constant has a value greater than or equal to 0.08, and less than or equal to 0.12.

14. The system of claim 11, wherein identifying the optimal sharpening kernel comprises:
determining, for each repetition, a signal to noise ratio obtained by applying the sharpening kernel generated on that repetition to the plurality of analysis images; and
identifying the sharpening kernel from which a highest signal to noise ratio is obtained as the optimal sharpening kernel.

15. The system of claim 14, wherein determining, for each repetition, the signal to noise ratio comprises calculating a sharpness of the plurality of sharpened images obtained on that repetition.

16. The system of claim 11, wherein obtaining noise dependencies comprises obtaining a noise map based on subtracting a first image from the plurality of analysis images from a second image from the plurality of analysis images.

17. The system of claim 16, wherein:
obtaining noise dependencies comprises dividing the noise map into a plurality of units, wherein each unit is a matrix of values having dimensions at least as great as those of the point spread function;
for each location in the point spread function, obtaining the noise dependency for that location comprises calculating a correlation between a first set of values and a second set of values, wherein:
the first set of values comprises, for each unit from the plurality of units, a value at a first location in that unit; and
the second set of values comprises, for each unit from the plurality of units, a value at a second location in that unit, wherein the first location for the value from that unit in the first set of values has a position relative to the second location that is the same as that location's position in the point spread function relative to the center of the point spread function.

18. The system of claim 16, wherein:
the first image from the plurality of analysis images is an image from a first sequencing cycle; and
the second image from the plurality of analysis images is an image from a second sequencing cycle.

19. The system of claim 11, wherein:
each image from the plurality of analysis images comprises an image from a different sequencing cycle;
the plurality of analysis images comprises more than two images;
obtaining noise dependencies comprises:
obtaining a plurality of intermediate correlations, wherein each of the intermediate correlations corresponds to two analysis images from the plurality of analysis images, and wherein each of the plurality of intermediate correlations is obtained based on:
obtaining an intermediate map for that intermediate correlation by subtracting one of the analysis images corresponding to that intermediate correlation from the other analysis image corresponding to that intermediate correlation;
dividing the intermediate map for that intermediate correlation into a plurality of units, wherein each unit is a matrix of values having dimensions at least as great as those of the point spread function;
for each location in the point spread function, calculating a correlation between a first set of values and a second set of values, wherein:
the first set of values comprises, for each unit from the plurality of units, a value at a first location in that unit; and
the second set of values comprises, for each unit from the plurality of units, a value at a second location in that unit, wherein the first location for the value from that unit in the first set of values has a position relative to the second location that is the same as that location's position in the point spread function relative to the center of the point spread function;
determining the set of noise dependencies based on the plurality of intermediate correlations.

* * * * *